(12) United States Patent
Liu et al.

(10) Patent No.: US 12,635,955 B2
(45) Date of Patent: May 26, 2026

(54) ELECTROENCEPHALOGRAM SIGNAL CLASSIFICATION METHOD AND APPARATUS, DEVICE, STORAGE MEDIUM, AND PROGRAM PRODUCT

(71) Applicant: Tencent Technology (Shenzhen) Company Limited, Shenzhen (CN)

(72) Inventors: Luyan Liu, Shenzhen (CN); Kai Ma, Shenzhen (CN); Yefeng Zheng, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 803 days.

(21) Appl. No.: 17/992,759

(22) Filed: Nov. 22, 2022

(65) Prior Publication Data

US 2023/0080533 A1     Mar. 16, 2023

Related U.S. Application Data

(63) Continuation of application No. PCT/CN2022/077714, filed on Feb. 24, 2022.

(30) Foreign Application Priority Data

Mar. 1, 2021     (CN) .......................... 202110226467.8

(51) Int. Cl.
    *A61B 5/00*          (2006.01)
    *A61B 5/372*         (2021.01)
(52) U.S. Cl.
    CPC ............ *A61B 5/7267* (2013.01); *A61B 5/372* (2021.01)
(58) Field of Classification Search
    CPC ...... A61B 5/7267; A61B 5/372; G16H 20/30; G16H 30/40; G16H 50/20; G16H 50/70
    See application file for complete search history.

(56) References Cited

U.S. PATENT DOCUMENTS

2015/0088024 A1     3/2015   Sackellares et al.

FOREIGN PATENT DOCUMENTS

CN          103413050 A      11/2013
CN          103425249 A      12/2013
                (Continued)

OTHER PUBLICATIONS

Rongrong Fu, Weishuai Li, Junxiang Chen, Mengmeng Han, "Recognizing single-trial motor imagery EEG based on interpretable clustering method", Biomedical Signal Processing and Control, (Year: 2020).*

(Continued)

*Primary Examiner* — Abid A Mustansir
(74) *Attorney, Agent, or Firm* — Morgan, Lewis & Bockius LLP

(57)          ABSTRACT

An electroencephalogram signal classification method includes: obtaining a first electroencephalogram signal; processing the first electroencephalogram signal using at least two electroencephalogram signal classification models to obtain respective motor imagery probability distributions from the at least two electroencephalogram signal classification models; and determining a motor imagery type of the first electroencephalogram signal based on the motor imagery probability distributions. A plurality of electroencephalogram signal classification models is respectively trained using an augmented data set obtained through augmentation. During prediction, by combining the plurality of electroencephalogram signal classification models, the accuracy of classifying an electroencephalogram signal to determine a motor imagery type may be improved, when using a model trained with a relatively small number of training samples.

18 Claims, 8 Drawing Sheets

(56)          References Cited

FOREIGN PATENT DOCUMENTS

| | | | |
|---|---|---|---|
| CN | 107550491 | A | 1/2018 |
| CN | 109730818 | A | 5/2019 |
| CN | 110414548 | A | 11/2019 |
| CN | 111062250 | A | 4/2020 |
| CN | 111728609 | A | 10/2020 |
| CN | 111832416 | A | 10/2020 |
| CN | 112270255 | A | 1/2021 |
| CN | 113712573 | A | 11/2021 |
| WO | WO 2020006263 | A1 | 1/2020 |

OTHER PUBLICATIONS

Tencent Technology, WO, PCT/CN2022/077714, May 11, 2022, 5 pgs.
Tencent Technology, IPRP, PCT/CN2022/077714, Aug. 29, 2023, 6 pgs.
Tencent Technology, ISR, PCT/CN2022/077714, May 11, 2022, 3 pgs.

* cited by examiner

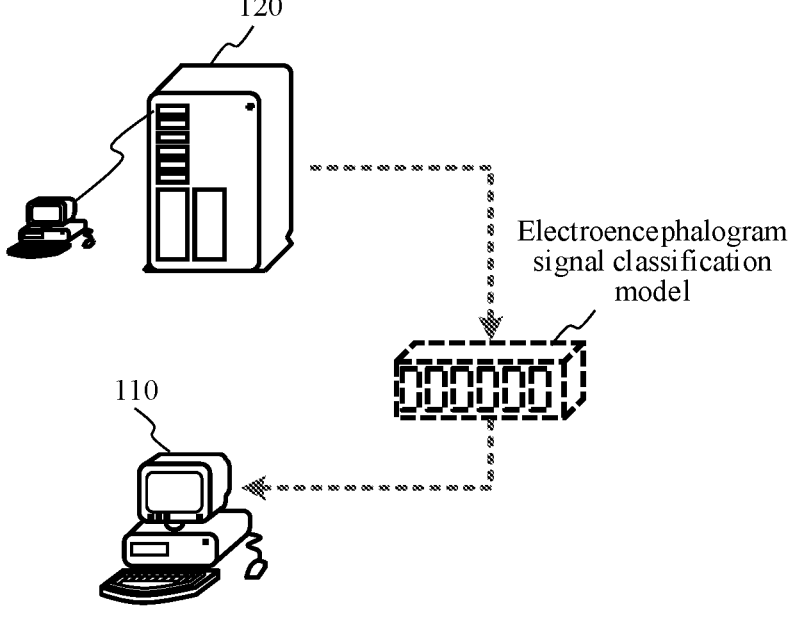

FIG. 1

| | 201 |
|---|---|
| Obtain a first electroencephalogram signal | |

| | 202 |
|---|---|
| Process, using at least two electroencephalogram signal classification models, the first electroencephalogram signal to obtain motor imagery probability distributions from the at least two electroencephalogram signal classification models | |

| | 203 |
|---|---|
| Determine a motor imagery type of the first electroencephalogram signal based on the motor imagery probability distributions | |

ELECTROENCEPHALOGRAM SIGNAL CLASSIFICATION METHOD AND APPARATUS, DEVICE, STORAGE MEDIUM, AND PROGRAM PRODUCT

CROSS-REFERENCE TO RELATED APPLICATIONS

This application is a continuation application of PCT Patent Application No. PCT/CN2022/077714, entitled "EEG SIGNAL CLASSIFICATION METHODS, DEVICES, DEVICES, STORAGE MEDIA AND PRO-GRAM PRODUCTS" filed on Feb. 24, 2022, which claims priority to Chinese Patent Application No. 202110226467.8, filed with the State Intellectual Property Office of the People's Republic of China on Mar. 1, 2021, and entitled "ELECTROENCEPHALOGRAM SIGNAL CLASSIFICA-TION METHOD AND APPARATUS, DEVICE, AND STORAGE MEDIUM", all of which are incorporated herein by reference in their entirety.

FIELD OF THE TECHNOLOGY

This application relates to the field of information pro-cessing technologies, and in particular, to an electroencepha-logram signal classification method and apparatus, a device, a storage medium, and a program product.

BACKGROUND OF THE DISCLOSURE

An electroencephalogram (EEG) is used to record the electrical wave changes during brain activity, which is a general reflection of the electrophysiological activity of brain nerve cells on the surface of the cerebral cortex or scalp.

In the related art, a motor imagery-brain-computer inter-face (MI-BCI) system has wide application prospects in many fields, and can control an external device with an electroencephalogram signal generated by a body movement imagined by the brain without any body movement. Motor imagery (MI) signal classification and recognition is the key link in the MI-BCI system, and the decoding accuracy of the MI signal classification and recognition directly affects the performance and user experience of the system.

SUMMARY

Embodiments of this application provide an electroen-cephalogram signal classification method and apparatus, a device, a storage medium, and a program product. The technical solution is as follows:

According to an aspect, an electroencephalogram signal classification method is provided, performed by a computer device, the method including:

obtaining a first electroencephalogram signal;

processing, using at least two electroencephalogram sig-nal classification models, the first electroencephalo-gram signal to obtain respective motor imagery prob-ability distributions from the at least two electroencephalogram signal classification models, wherein each electroencephalogram signal classifica-tion model is a machine learning model trained using an augmented data set; and determining a motor imagery type of the first electroen-cephalogram signal based on the motor imagery prob-ability distributions including obtaining a motor imag-ery probability distribution of the first electroencephalogram signal based on the motor imag-ery probability distributions from the at least two electroencephalogram signal classification models, the motor imagery probability distribution of the first elec-troencephalogram signal comprising probability values corresponding to respective motor imagery types According to an aspect, an electroencephalogram signal classification method is provided, performed by a computer device, the method including:

obtaining a first electroencephalogram signal;

processing, using at least two electroencephalogram sig-nal classification models, the first electroencephalo-gram signal to obtain respective motor imagery prob-ability distributions from the at least two electroencephalogram signal classification models, each electroencephalogram signal classification model being a machine learning model trained using an aug-mented data set, the augmented data set being a data set obtained by performing data augmentation on a training sample subset, the training sample subset including a sample electroencephalogram signal other than (e.g., different from) a verification electroencephalogram sig-nal of the electroencephalogram signal classification model in a first training sample set, the first training sample set including at least two sample electroen-cephalogram signals and motor imagery types of the at least two sample electroencephalogram signals, the verification electroencephalogram signal being a sample electroencephalogram signal used for verifying the electroencephalogram signal classification model, the at least two electroencephalogram signal classifi-cation models having different verification electroen-cephalogram signals in the first training sample set; and determining a motor imagery type of the first electroen-cephalogram signal based on the respective motor imagery probability distributions.

According to another aspect, an electroencephalogram signal classification method is provided, performed by a computer device, the method including:

obtaining a first training sample set, the first training sample set including at least two sample electroen-cephalogram signals and motor imagery types of the at least two sample electroencephalogram signals;

obtaining respective training sample subsets of at least two electroencephalogram signal classification models based on the first training sample set, each training sample subset including a sample electroencephalo-gram signal different from a verification electroen-cephalogram signal of each electroencephalogram sig-nal classification model in the first training sample set, the first training sample set including the at least two sample electroencephalogram signals and the motor imagery types of the at least two sample electroen-cephalogram signals, the verification electroencepha-logram signal being a sample electroencephalogram signal used for verifying the electroencephalogram signal classification model, the at least two electroen-cephalogram signal classification models having dif-ferent verification electroencephalogram signals in the first training sample set; and training respective electroencephalogram signal classifi-cation models of at least two training sample subsets based on at least two augmented data sets to obtain at least two trained electroencephalogram signal classifi-cation models, the at least two augmented data sets being data sets obtained by performing data augmentation on the respective training sample subsets of the at least two electroencephalogram signal classification models, where the at least two trained electroencephalogram signal classification models are configured to perform data processing on a first electroencephalogram signal to obtain respective motor imagery probability distributions from the at least two electroencephalogram signal classification models, the motor imagery probability distributions from the at least two electroencephalogram signal classification models being used for determining a motor imagery type of the first electroencephalogram signal.

According to still another aspect, an electroencephalogram signal classification apparatus is provided, including:

an electroencephalogram signal obtaining module, configured to obtain a first electroencephalogram signal;

a probability distribution obtaining module, configured to process the first electroencephalogram signal respectively using at least two electroencephalogram signal classification models to obtain respective motor imagery probability distributions from the at least two electroencephalogram signal classification models, each electroencephalogram signal classification model being a machine learning model trained using an augmented data set, the augmented data set being a data set obtained by performing data augmentation on a training sample subset, the training sample subset including a sample electroencephalogram signal different from a verification electroencephalogram signal of the electroencephalogram signal classification model in a first training sample set, the first training sample set including at least two sample electroencephalogram signals and motor imagery types of the at least two sample electroencephalogram signals, the verification electroencephalogram signal being a sample electroencephalogram signal used for verifying the electroencephalogram signal classification model, the at least two electroencephalogram signal classification models respectively having different verification electroencephalogram signals in the first training sample set; and a motor imagery type obtaining module, configured to determine a motor imagery type of the first electroencephalogram signal based on the motor imagery probability distributions.

According to still another aspect, an electroencephalogram signal classification apparatus is provided, including:

a training subset obtaining module, configured to obtain a first training sample set, the first training sample set including at least two sample electroencephalogram signals and motor imagery types of the at least two sample electroencephalogram signals;

a training sample subset obtaining module, configured to obtain respective training sample subsets of at least two electroencephalogram signal classification models based on the first training sample set, each training sample subset including a sample electroencephalogram signal other than a verification electroencephalogram signal of each electroencephalogram signal classification model in the first training sample set, the first training sample set including the at least two sample electroencephalogram signals and the motor imagery types of the at least two sample electroencephalogram signals, the verification electroencephalogram signal being a sample electroencephalogram signal used for verifying the electroencephalogram signal classification model, the at least two electroencephalogram signal classification models respectively having different verification electroencephalogram signals in the first training sample set; and a model training module, configured to train respective electroencephalogram signal classification models of at least two training sample subsets based on at least two augmented data sets to obtain at least two trained electroencephalogram signal classification models, the at least two augmented data sets being data sets obtained by performing data augmentation on the respective training sample subsets of the at least two electroencephalogram signal classification models, where the at least two trained electroencephalogram signal classification models are configured to perform data processing on a first electroencephalogram signal to obtain respective motor imagery probability distributions from the at least two electroencephalogram signal classification models, the motor imagery probability distributions from the at least two electroencephalogram signal classification models being used for determining a motor imagery type of the first electroencephalogram signal.

According to still another aspect, a computer device is provided, including a processor and a memory, the memory storing at least one computer instruction, the at least one computer instruction being loaded and executed by the processor to implement the foregoing electroencephalogram signal classification method.

According to still another aspect, a computer-readable storage medium is provided, the storage medium storing at least one computer instruction, the at least one computer instruction being loaded and executed by a processor to implement the foregoing electroencephalogram signal classification method.

According to still another aspect, a computer program product or a computer program is provided, the computer program product or the computer program including computer instructions, the computer instructions being stored in a computer-readable storage medium. A processor of a computer device reads the computer instructions from the computer-readable storage medium, and executes the computer instructions, so that the computer device performs the foregoing electroencephalogram signal classification method.

In the technical solution provided in the embodiments of this application, a plurality of electroencephalogram signal classification models are trained based on augmented data sets obtained by performing data augmentation on different training subsets of the same training sample set, an electroencephalogram signal is processed using the plurality of trained electroencephalogram signal classification models to obtain respective probability distributions from the plurality of electroencephalogram signal classification models, and a motor imagery type of the electroencephalogram signal is determined according to the respective probability distributions from the plurality of electroencephalogram signal classification models. In the foregoing solution, different sample subsets are obtained from one training sample set, and at least two electroencephalogram signal classification models are trained after data augmentation. In a prediction process, the same electroencephalogram signal is classified respectively using the at least two electroencephalogram signal classification models, so that a motor imagery type of the electroencephalogram signal is obtained by combining respective output results of the at least two electroencephalogram signal classification models. That is, for a relatively small number of training samples, a training sample set is divided into a plurality of subsets before data augmentation. A plurality of electroencephalogram signal classification models is respectively trained using an augmented data set obtained through augmentation. During prediction, a motor imagery type is respectively determined for an output result of an electroencephalogram signal by combining the plurality of electroencephalogram signal classification models, and may improve the accuracy of classifying an electroencephalogram signal using a model trained with a relatively small number of training samples.

BRIEF DESCRIPTION OF THE DRAWINGS

FIG. 1 is a schematic diagram of a computer system according to an exemplary embodiment of this application.

FIG. 2 is a schematic flowchart of an electroencephalogram signal classification method according to an exemplary embodiment.

DESCRIPTION OF EMBODIMENTS

Figures 3, 4:
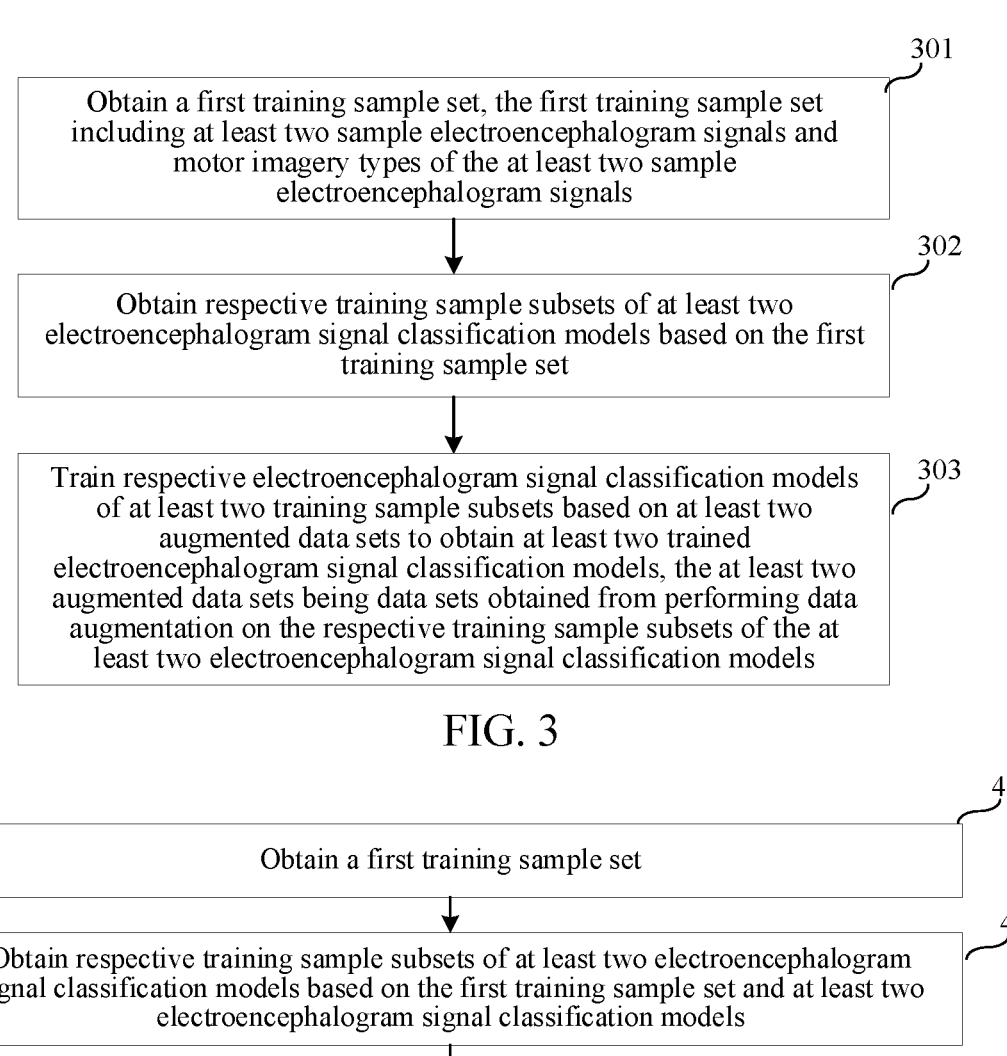
FIG. 3 is a schematic flowchart of an electroencephalogram signal classification method according to an exemplary embodiment.
FIG. 4 is a method flowchart of an electroencephalogram signal classification method according to an exemplary embodiment.

The electroencephalogram signal classification method provided in the embodiments of this application is applicable to a computer device having a data processing capability. In a possible embodiment, the electroencephalogram signal classification method provided in the embodiments of this application is applicable to a personal computer, a workstation, or a server. That is, an electroencephalogram signal classification model may be trained using a personal computer, a workstation, or a server. In a possible embodiment, an electroencephalogram signal classification model trained using the electroencephalogram signal classification method provided in the embodiments of this application is applicable to the classification of an electroencephalogram signal, that is, the data processing of an electroencephalogram signal generated by the brain during the obtained human motor imagery, to obtain a motor imagery type of the electroencephalogram signal.

FIG. 1 is a schematic diagram of a computer system according to an exemplary embodiment of this application. The computer system includes a terminal 110 and a server

120. The terminal 110 is in data communication with the server 120 through a communication network. In some embodiments, the communication network may be a wired network or a wireless network, and the communication network may be at least one of a local area network, a metropolitan area network, and a wide area network.

An application with an electroencephalogram signal processing function is installed on the terminal 110. The application may be a virtual reality application, a game application or an artificial intelligence (AI) application with an electroencephalogram signal processing function. This is not limited in the embodiments of this application.

In some embodiments, the terminal device 110 may be a terminal device with a brain-computer interface. The brain-computer interface may obtain an electroencephalogram signal from the brain of a target object through an electrode; or the computer device includes a data transmission interface, and the data transmission interface is configured to receive an electroencephalogram signal acquired by a data acquisition device with a brain-computer interface.

In some embodiments, the terminal device 110 may be a mobile terminal such as a smartphone, a tablet computer, a portable laptop computer, or may be a terminal such as a desktop computer or a projection computer, or a smart terminal with a data processing component. This is not limited in the embodiments of this application.

The server 120 may be implemented as a server or may be implemented as a server cluster formed by a set of servers, and may be a physical server or may be implemented as a cloud server. In a possible embodiment, the server 120 is a backend server of the application in the terminal device 110.

In a possible embodiment of this embodiment, the server 120 trains an electroencephalogram signal classification model using a preset training sample set (that is, sample electroencephalogram signals). The training sample set may include sample electroencephalogram signals of various motor imagery types. After completing a training process of the electroencephalogram signal classification model, the server 120 transmits the trained electroencephalogram signal classification model to the terminal 110 through a wired or wireless connection. The terminal 110 receives the trained electroencephalogram signal classification model, and inputs data information of the electroencephalogram signal classification model into the application with an electroencephalogram signal processing function, so that when a user uses the application to process an electroencephalogram signal, the electroencephalogram signal may be processed according to the trained electroencephalogram signal classification model, to implement all or some steps of the electroencephalogram signal classification method.

FIG. 2 is a schematic flowchart of an electroencephalogram signal classification method according to an exemplary embodiment. The method may be performed by a computer device. The computer device may be the foregoing terminal 110 or server 120 in the embodiment shown in FIG. 1. As shown in FIG. 2, a procedure of the electroencephalogram signal classification method may include the following steps:

Step 201: Obtain a first electroencephalogram signal.

In a possible embodiment, the first electroencephalogram signal is an electroencephalogram signal of a target object acquired by a device with a brain-computer interface. The brain-computer interface includes at least two electrodes. In a process of acquiring a signal from the target object using the brain-computer interface, the two electrodes are arranged in different areas of the brain of the target object to acquire electroencephalogram signals generated in the different areas of the target object.

Step 202: Process the first electroencephalogram signal respectively using at least two electroencephalogram signal classification models to obtain respective motor imagery probability distributions from the at least two electroencephalogram signal classification models.

Each electroencephalogram signal classification model is a machine learning model trained using an augmented data set. The augmented data set is a data set by performing data augmentation on a training sample subset. The training sample subset includes a sample electroencephalogram signal other than (e.g., different from) a verification electroencephalogram signal of the electroencephalogram signal classification model in a first training sample set. The first training sample set includes at least two sample electroencephalogram signals and motor imagery types of the at least two sample electroencephalogram signals. The verification electroencephalogram signal is a sample electroencephalogram signal used for verifying the electroencephalogram signal classification model. The at least two electroencephalogram signal classification models respectively have different verification electroencephalogram signals in the first training sample set.

Step 203: Determine a motor imagery type of the first electroencephalogram signal based on the respective motor imagery probability distributions from the at least two electroencephalogram signal classification models.

In summary, in the solution in the embodiments of this application, a plurality of electroencephalogram signal classification models are trained based on augmented data sets by performing data augmentation on different training subsets of the same training sample set, an electroencephalogram signal is processed using the plurality of trained electroencephalogram signal classification models to obtain probability distributions outputted by the plurality of electroencephalogram signal classification models, and a motor imagery type of the electroencephalogram signal is determined according to the probability distributions outputted by the plurality of electroencephalogram signal classification models. In the foregoing solution, different sample subsets are obtained from one training sample set, and at least two electroencephalogram signal classification models are trained after data augmentation. In a prediction process, the same electroencephalogram signal is classified respectively using the at least two electroencephalogram signal classification models, so that a motor imagery type of the electroencephalogram signal is obtained by combining respective output results of the at least two electroencephalogram signal classification models. That is, for a relatively small number of training samples, a training sample set is divided into a plurality of subsets before data augmentation. A plurality of electroencephalogram signal classification models are respectively trained using an augmented data set obtained through augmentation. During prediction, a motor imagery type is respectively determined for an output result of an electroencephalogram signal by combining the plurality of electroencephalogram signal classification models, thereby improving the accuracy of classifying an electroencephalogram signal using a model trained with a relatively small number of training samples.

FIG. 3 is a schematic flowchart of an electroencephalogram signal classification method according to an exemplary embodiment. The method may be performed by a computer device. The computer device may be the foregoing terminal 110 or server 120 in the embodiment shown in FIG. 1. As shown in FIG. 3, a procedure of the electroencephalogram signal classification method may include the following steps:

Step 301: Obtain a first training sample set, the first training sample set including at least two sample electroencephalogram signals and motor imagery types of the at least two sample electroencephalogram signals.

Step 302: Obtain respective training sample subsets of at least two electroencephalogram signal classification models based on the first training sample set.

Training sample subsets that respectively correspond to at least two electroencephalogram signal classification models are obtained based on the first training sample set and at least two electroencephalogram signal classification models.

The training sample subset includes a sample electroencephalogram signal other than a verification electroencephalogram signal of the electroencephalogram signal classification model in a first training sample set. The at least two electroencephalogram signal classification models have different respectively sample electroencephalogram signals in the first training sample set. The first training sample set includes at least two sample electroencephalogram signals and motor imagery types of the at least two sample electroencephalogram signals. The verification electroencephalogram signal is a sample electroencephalogram signal used for verifying the electroencephalogram signal classification model. The at least two electroencephalogram signal classification models respectively have different verification electroencephalogram signals in the first training sample set.

Step 303: Respectively train respective electroencephalogram signal classification models of at least two training sample subsets based on at least two augmented data sets to obtain at least two trained electroencephalogram signal classification models, the at least two augmented data sets being data sets obtained by performing data augmentation on the respective training sample subsets of the at least two electroencephalogram signal classification models.

The at least two trained electroencephalogram signal classification models are configured to perform data processing on a first electroencephalogram signal to obtain respective motor imagery probability distributions from the at least two electroencephalogram signal classification models. The motor imagery probability distributions from the at least two electroencephalogram signal classification models are used for determining a motor imagery type of the first electroencephalogram signal.

In summary, in the solution in the embodiments of this application, a plurality of electroencephalogram signal classification models are trained based on augmented data sets obtained by performing data augmentation on different training subsets of the same training sample set, an electroencephalogram signal is processed using the plurality of trained electroencephalogram signal classification models to obtain probability distributions outputted by the plurality of electroencephalogram signal classification models, and a motor imagery type of the electroencephalogram signal is determined according to the probability distributions outputted by the plurality of electroencephalogram signal classification models. In the foregoing solution, different sample subsets are obtained from one training sample set, and at least two electroencephalogram signal classification models are trained after data augmentation. In a prediction process, the same electroencephalogram signal is classified respectively using the at least two electroencephalogram signal classification models, so that a motor imagery type of the electroencephalogram signal is obtained by combining respective output results of the at least two electroencephalogram signal classification models. That is, for a relatively small number of training samples, a training sample set is divided into a plurality of subsets before data augmentation. A plurality of electroencephalogram signal classification models are respectively trained using an augmented data set obtained through augmentation. During prediction, a motor imagery type is respectively determined for an output result of an electroencephalogram signal by combining the plurality of electroencephalogram signal classification models, thereby improving the accuracy of classifying an electroencephalogram signal using a model trained with a relatively small number of training samples.

FIG. 4 is a method flowchart of an electroencephalogram signal classification method according to an exemplary embodiment. The method may be jointly performed a model training device and a signal processing device. The model training device may be the foregoing terminal 110 or server 120 in the embodiment shown in FIG. 1. The signal processing device may be the foregoing terminal 110 or server 120 in the embodiment shown in FIG. 1. As shown in FIG. 4, a procedure of the electroencephalogram signal classification method may include the following steps:

Step 401: Obtain a first training sample set.

The first training sample set includes at least two sample electroencephalogram signals and motor imagery types of the at least two sample electroencephalogram signals.

In a possible embodiment, each sample electroencephalogram signal includes at least two sample electrode signals.

The at least two sample electrode signals may be electroencephalogram signals that are generated in the brain of a sample target object during motor imagery and are obtained by a terminal device with a brain-computer interface using electrodes of the brain-computer interface. A quantity of the sample electrode signals is the same as a quantity of the electrodes of the brain-computer interface. That is, the brain-computer interface may use different electrodes to obtain electroencephalogram signals generated in different spatial areas in the brain of the same sample target object during motor imagery.

In a possible embodiment, the brain-computer interface uses the electrodes to obtain electroencephalogram signals generated in different areas in the brain of a sample target object, and the electrodes transmit the electroencephalogram signals of the electrodes to a terminal device equipped with the brain-computer interface through a transmission line.

In a possible embodiment, the terminal device may obtain, based on the electrodes of the brain-computer interface, an original sample electroencephalogram signal generated in the brain of the sample target object during motor imagery; and perform filtering with a band-pass filter based on the original sample electroencephalogram signal to obtain the first sample electroencephalogram signal.

Because there is considerable noise interference in the original sample electroencephalogram signal obtained by the electrodes of the brain-computer interface, it is necessary to first filter the original sample electroencephalogram signal with a band-pass filter to reduce the impact of irrelevant noise on the electroencephalogram signal.

For example, the terminal device performs 3- to 38-Hz band-pass filtering on each original sample electroencephalogram signal to eliminate the impact of irrelevant physiological noise from eye movement or the like and utility frequency interference (that is, interference caused by the power system, and the frequency is generally 50 Hz) on the EEG signal.

Step 402: Obtain respective training sample subsets of at least two electroencephalogram signal classification models based on the first training sample set and at least two electroencephalogram signal classification models.

The training sample subset includes a sample electroencephalogram signal different from a verification electroencephalogram signal of the electroencephalogram signal classification model in a first training sample set. The at least two electroencephalogram signal classification models have different respectively sample electroencephalogram signals in the first training sample set. The first training sample set includes at least two sample electroencephalogram signals and motor imagery types of the at least two sample electroencephalogram signals. The verification electroencephalogram signal is a sample electroencephalogram signal in the at least two sample electroencephalogram signals that is used for verifying the electroencephalogram signal classification model. The at least two electroencephalogram signal classification models respectively have different verification electroencephalogram signals in the first training sample set.

In a possible embodiment, in response to that the at least two training sample subsets include a first training sample subset, the first training sample set is obtained; and a first training sample subset is obtained based on a sample electroencephalogram signal different from a verification electroencephalogram signal of the first electroencephalogram signal classification model in the first training sample set, respective sample electroencephalogram signals of the electroencephalogram signal classification models are different in the first training sample set.

Before the electroencephalogram signal classification models are trained, some sample electroencephalogram signals of the electroencephalogram signal classification models may be selected from the first training sample set and used as verification electroencephalogram signals of the electroencephalogram signal classification models, to verify a trained electroencephalogram signal classification model to determine whether the training of the electroencephalogram signal classification model is completed.

In addition, for any electroencephalogram signal classification model, a sample electroencephalogram signal different from a verification electroencephalogram signal of the electroencephalogram signal classification model in the first training sample set may be used as a training sample of the electroencephalogram signal classification model to train the electroencephalogram signal classification model.

In a possible embodiment, the verification electroencephalogram signal of the electroencephalogram signal classification model may be one in the sample electroencephalogram signals; or the verification electroencephalogram signal of the electroencephalogram signal classification model may be a plurality of signals in the sample electroencephalogram signals. In this case, the electroencephalogram signal classification model may obtain sample electroencephalogram signals different from plurality of verification electroencephalogram signals in the first training sample set as a training sample subset of the electroencephalogram signal classification model, and training based on the training sample subset. An electroencephalogram signal classification model that has been trained predetermined rounds may be verified by the verification electroencephalogram signal.

In a possible embodiment, the computer device determines respective verification electroencephalogram signals of the at least two electroencephalogram signal classification models from at least two sample electroencephalogram signals in the first training sample set based on the at least two electroencephalogram signal classification models; and obtain the respective training sample subsets of the at least two electroencephalogram signal classification models based on the respective verification electroencephalogram signals of the at least two electroencephalogram signal classification models and the first training sample set.

In a possible embodiment, in response to that the at least two electroencephalogram signal classification models include a first electroencephalogram signal classification model, the computer device determines the verification electroencephalogram signal of the first electroencephalogram signal classification model from the at least two sample electroencephalogram signals in the first training sample set based on the first electroencephalogram signal classification model.

The first training sample subset is one of the subsets of the first training sample set, and the first training sample subset is used for training the first electroencephalogram signal classification model.

In the first training sample set, for each electroencephalogram signal classification model, a verification sample electroencephalogram signal of the electroencephalogram signal classification model is determined, and other sample electroencephalogram signals different from the verification sample electroencephalogram signal of the electroencephalogram signal classification model in the first training sample set are determined as a training sample subset of the electroencephalogram signal classification model, so that after training using the training sample subset, the electroencephalogram signal classification model may be verified using the verification sample electroencephalogram signal.

Figure 5:
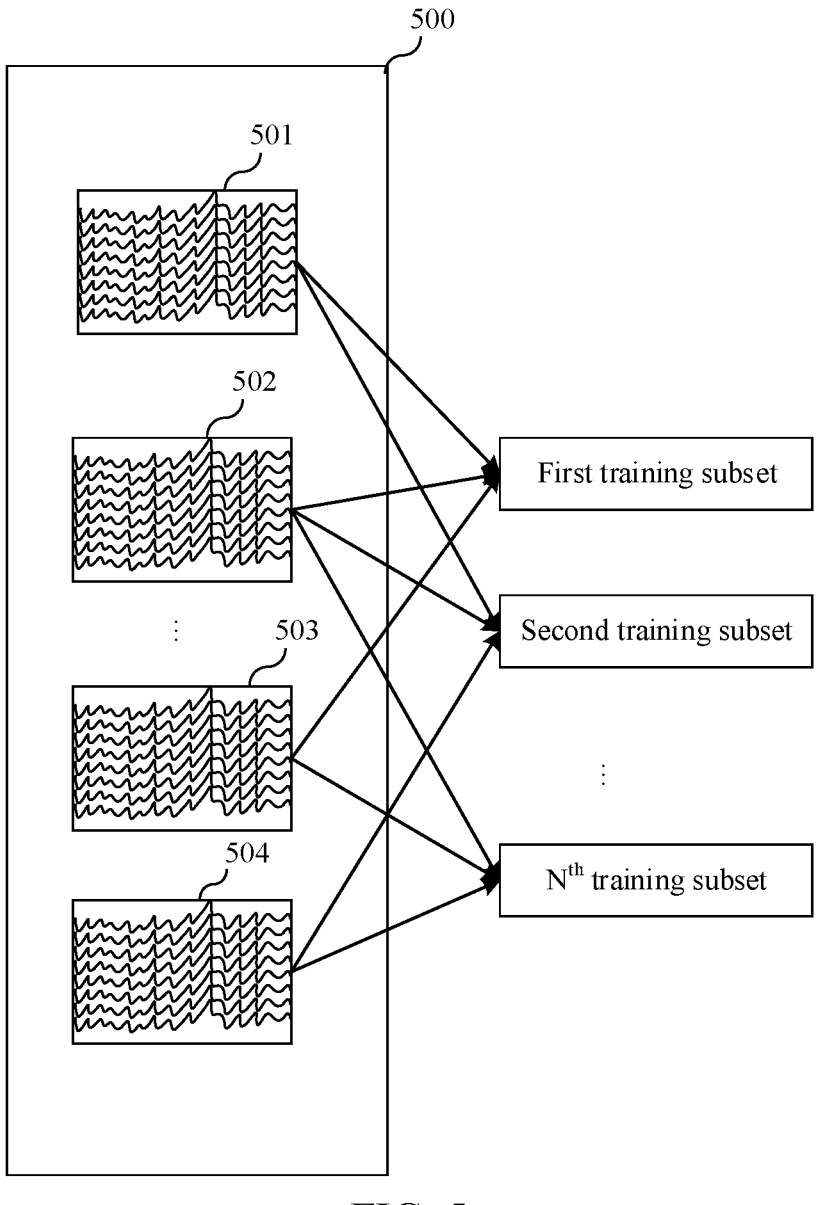
FIG. 5 is a schematic diagram of obtaining a training sample subset in the embodiment shown in FIG. 4.

FIG. 5 is a schematic diagram of obtaining a training sample subset in the embodiment of this application. As shown in FIG. 5, a first training sample set 500 includes a first sample electroencephalogram signal 501, a second sample electroencephalogram signal 502, . . . , an $(N-1)^{th}$ sample electroencephalogram signal 503, and an $N^{th}$ sample electroencephalogram signal 504. In this case, for the first electroencephalogram signal classification model, the $N^{th}$ sample electroencephalogram signal 504 is used as a verification electroencephalogram signal of the first electroencephalogram signal classification model. In this case, the first sample electroencephalogram signal 501, the second sample electroencephalogram signal 502, . . . , and the $(N-1)^{th}$ sample electroencephalogram signal 503 forms the first training sample subset of the first electroencephalogram signal classification model. In this case, for a second electroencephalogram signal classification model, the $(N-1)^{th}$ sample electroencephalogram signal 503 may be used as a verification electroencephalogram signal of the second electroencephalogram signal classification model. In this case, the first sample electroencephalogram signal 501, the second sample electroencephalogram signal 502, . . . , an $(N-2)^{th}$ sample electroencephalogram signal, and the $N^{th}$ sample electroencephalogram signal 504 forms a second training sample subset of the second electroencephalogram signal classification model. Other training sample subsets may be obtained in a similar manner. Details are not described herein again.

Step 403: Train respective electroencephalogram signal classification models of at least two training sample subsets based on at least two augmented data sets obtained by performing data augmentation based on the at least two training sample subsets to obtain at least two trained electroencephalogram signal classification models.

The at least two trained electroencephalogram signal classification models are configured to perform data processing on a first electroencephalogram signal to obtain probability distributions of the first electroencephalogram signal that respectively correspond to the at least two electroencephalogram signal classification models. The probability distributions of the first electroencephalogram signal that respectively correspond to the at least two electroencephalogram signal classification models may be used for determining a motor imagery type of the first electroencephalogram signal.

Before the at least two electroencephalogram signal classification models are trained using the at least two training sample subsets, data augmentation may be performed first to expand sample electroencephalogram signals in the at least two training sample subsets, to increase a quantity of samples included in each training sample subset, thereby improving the effect of training an electroencephalogram signal classification model.

In a possible embodiment, the first training sample set is obtained; a first training sample subset is obtained based on a sample electroencephalogram signal different from a verification electroencephalogram signal of the first electroencephalogram signal classification model in the first training sample set, the first training sample subset including a first sample electroencephalogram signal; performing data augmentation based on the first training sample subset to obtain a first augmented data set, the first augmented data set including the first sample electroencephalogram signal, a first augmented signal of the first sample electroencephalogram signal, and a motor imagery type of the first sample electroencephalogram signal; and the first electroencephalogram signal classification model is trained based on the first augmented data set.

When the first electroencephalogram signal classification model in the at least two electroencephalogram signal classification models needs to be trained, a training sample subset of the first electroencephalogram signal classification model may be determined according to the first electroencephalogram signal classification model, and performing data augmentation according to the training sample subset of the first electroencephalogram signal classification model to obtain a first augmented data set, the first augmented data set including the first sample electroencephalogram signal, a first augmented signal of the first sample electroencephalogram signal, and a motor imagery type of the first sample electroencephalogram signal. In this case, the first electroencephalogram signal classification model may be trained using the first sample electroencephalogram signal as a sample and the motor imagery type of the first sample electroencephalogram signal as a label, or the first electroencephalogram signal classification model may be trained using the first augmented signal of the first sample electroencephalogram signal is used as a sample and the motor imagery type of the first sample electroencephalogram signal as a label.

Alternatively, the computer device may first obtain training sample subsets through division, perform data augmentation according to the at least two training sample subsets obtained through division to obtain at least two augmented data sets, and then respectively allocate the at least two augmented data sets to the electroencephalogram signal classification models.

In a possible embodiment, during data augmentation, the computer device may obtain an augmentation factor of the first training sample subset, the augmentation factor being used for indicating a scaling ratio of a sample in the training sample subset; scale the first sample electroencephalogram signal based on the augmentation factor of the first training sample subset to obtain the first augmented signal of the first sample electroencephalogram signal; and obtain the first augmented data set based on the first sample electroencephalogram signal, the first augmented signal, and the motor imagery type of the first sample electroencephalogram signal.

During augmentation of the first training sample subset, an augmentation factor of the first training sample subset needs to be obtained, and samples in the first training sample subset are scaled according to the augmentation factor, to obtain respective augmented data of sample electroencephalogram signals in the first training sample subset. After augmented data is obtained by scaling a sample electroencephalogram signal, a motor imagery type of the augmented data is the same as a motor imagery type of the sample electroencephalogram signal. In this case, the augmented data set includes the sample electroencephalogram signal before scaling, the augmented data obtained through scaling, and the motor imagery type of the sample electroencephalogram signal.

In a possible embodiment of the embodiments of this application, data augmentation may be performed on the first training sample subset once to obtain the augmented data set of the first training sample subset. In this case, a quantity of samples in the augmented data set is twice that in the first training sample subset. Alternatively, data augmentation may be performed on the first training sample subset N times to obtain the augmented data set of the first training sample subset. In this case, a quantity of samples in the augmented data set is N times that in the first training sample subset.

For example, during data augmentation, in this solution, a data duplication and scaling technology is used to expand electroencephalogram data samples. First, electroencephalogram data samples used for training are first duplicated to obtain an augmented data set having training data consistent with original training data, and the augmented data set is labeled as dataset1. Each electroencephalogram sample in the training data set is multiplied by a scaling factor $\alpha=0.9$ to obtain an expanded data set dataset2. Each electroencephalogram sample in the training data set is multiplied by a scaling factor $\alpha=1.1$ to obtain an expanded data set dataset3. In this solution, alpha is used as the scaling factor, and the scaling factor is set to 0.9 and 1.1. A scaling factor of another value may be selected.

In a possible embodiment, the first electroencephalogram signal classification model includes a first channel attention weighting module, a first temporal convolutional layer, a first spatial convolutional layer, a first activation layer, and a first fully connected layer; processing the first sample electroencephalogram signal using the first channel attention weighting module to obtain a first sample weighted feature map; processing is performed based on the first sample weighted feature map using the first temporal convolutional layer to obtain a first sample temporal feature map, the first temporal convolutional layer being configured to extract a temporal feature of an electroencephalogram signal; processing is performed based on the first sample temporal feature map using the first spatial convolutional layer to obtain a first sample spatial feature map; the first spatial convolutional layer is configured to extract spatial features of different areas of the brain of an object of the electroencephalogram signal; data processing is performed based on the first sample spatial feature map using the first activation layer to obtain a first sample activation feature map; data processing is performed based on the first sample activation feature map using the first fully connected layer to obtain a probability distribution that is of the first sample electroencephalogram signal and is outputted by the first electroen- cephalogram signal classification model; and the first electroencephalogram signal classification model is trained based on the probability distribution of the first sample electroencephalogram signal and the motor imagery type of the first sample electroencephalogram signal.

A channel in the convolutional neural network may be used for indicating a feature map. The intensity of a point in the channel may represent the value at the point of the feature map. Different channels are used for indicating feature maps in different dimensions. For a feature map with a plurality of channels, the meaning of the channels is that the feature map has image features in a plurality of dimensions. There are two main operations, namely, convolution and pooling, in the convolutional network. The pooling layer performs an operation in the channels. The convolutional layer may perform interaction between channels, and then generate a new channel in a next layer.

In a possible embodiment, data processing is performed based on the first sample activation feature map using the first fully connected layer to obtain a feature vector of the first sample electroencephalogram signal, and a probability distribution that is of the first sample electroencephalogram signal and is outputted by the first electroencephalogram signal classification model is obtained based on the feature vector of the first sample electroencephalogram signal.

After data processing is performed on the first sample activation feature map using the first fully connected layer, the first fully connected layer may output the feature vector of the first sample electroencephalogram signal. In this case, the feature vector is normalized, so that a normalized feature vector with a sum of values in the dimensions being 1. In this case, the value in each dimension of the normalized feature vector respectively represents a probability of a motor imagery type. The values of the dimensions of the normalized feature vector together form the probability distribution of the first sample electroencephalogram signal.

Figure 6:
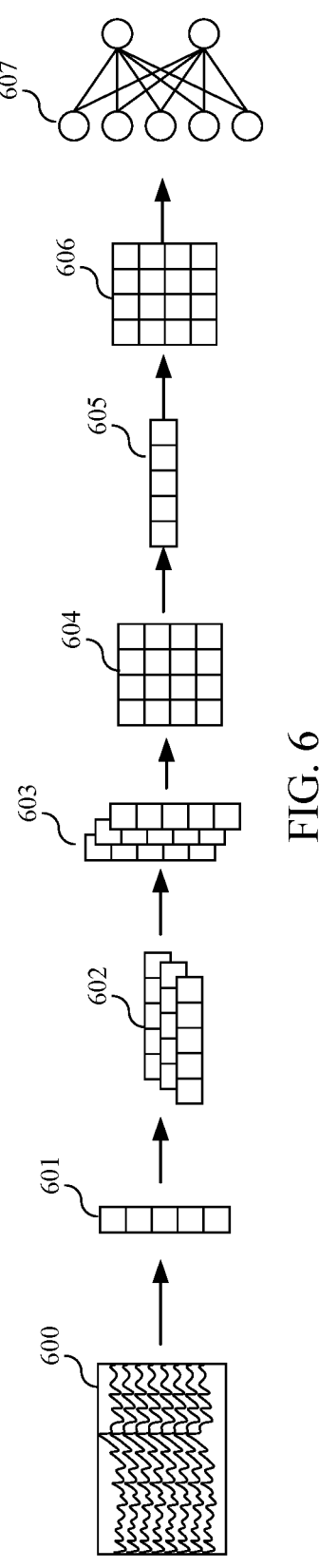
FIG. 6 is a schematic diagram of an electroencephalogram signal classification model in the embodiment shown in FIG. 4.

FIG. 6 is a schematic diagram of an electroencephalogram signal classification model in the embodiments of this application. As shown in FIG. 6, for the inputted first sample electroencephalogram signal 600, the first sample electroencephalogram signal 600 includes sample electrode signals of at least two electrodes. Channel weights of the electrodes of the first sample electroencephalogram signal may be obtained using a channel attention weighting module 601, and the sample electrode signals of the electrodes are weighted according to the channel weights of the electrodes to obtain a weighted first sample weighted feature map. The weighted first sample weighted feature map is processed using a first temporal convolutional layer 602 to obtain a first sample temporal feature map. As can be seen from a part 602 in FIG. 6, an arrangement manner of the convolution kernels of the first temporal convolutional layer is consistent with an acquisition time sequence of signals in the sample electrode signal. That is, during feature extraction of the sample electrode signal using the convolution kernels of the first temporal convolutional layer, features at different time points in each electrode signal may be fused to obtain a first sample temporal feature map including temporal features of the electrode signals. After the first sample temporal feature map is obtained, the first sample temporal feature map is processed using a first spatial convolutional layer 603. As can be seen from a part 603 in FIG. 6, each convolution kernel of the first spatial convolutional layer 603 may simultaneously perform feature extraction on a plurality of electrode signals. Extracted features simultaneously include features of the plurality of electrode signals. In addition, the electrode signals are acquired based on different spatial areas of the brain of a target object. Therefore, the first sample spatial feature map extracted using the first spatial convolutional layer 603 is fused with the spatial features of the electrode signals. After the first sample spatial feature map is obtained, a square operation may then be performed on each element in the extracted first sample spatial feature map using a square activation layer 604. A first sample activation feature map is then obtained after processing in a pooling layer 605 and a logarithmic activation layer 606. In this case, the first sample activation feature map is processed using a fully connected layer 607 to obtain a feature vector of the first sample electroencephalogram signal, and a motor imagery probability distribution of the first sample electroencephalogram signal is obtained according to the feature vector.

In this solution, a channel attention-based electroencephalogram decoding model is designed according to a temporal characteristic, a spatial characteristic, and a frequency characteristic of an EEG signal. The decoding model may include a channel attention layer, a temporal convolutional layer, a spatial convolutional layer, a normalization layer, a square activation layer, an average pooling layer, a logarithmic activation layer, and a fully connected layer. The size of a signal inputted into the network is 350×40 (40 is an electrode quantity, and 350 is a time length). The first layer is a channel attention layer Channel Attention, and generates a channel attention map according to the inputted signal. An attention weight is 1×40. A channel attention weight is generated using a fully connected layer with a hidden node of 5. The second layer is a temporal convolutional layer Temporal Cony. The size of the convolution kernel is 25×1, the strides are all 1, and the number of convolution channels is 20. The third layer is a spatial convolutional layer Spatial Cony. The size of the convolution kernel is 40×1, the strides are all 1, and the number of convolution channels is 20. The fourth layer is a normalization layer Batch Normalization, configured to increases the speed of model convergence. The fifth layer is a square activation layer. A square operation is performed on each element in the feature map, to enhance the expression capability of nonlinear features. The sixth layer is an average pooling layer (the kernel size is 35×1, and the stride is 15×1), performs size compression on a feature map, and performs nonlinear mapping on a feature map using a Log activation layer, then connects to a dropout layer Dropout, suppresses overfitting, and setting a dropout rate to 0.5. The last layer is a fully connected layer and is configured to fuse deep features. An output node of the fully connected layer is 2, and corresponds to the number of classes in electroencephalogram classification.

Figures 7, 8:
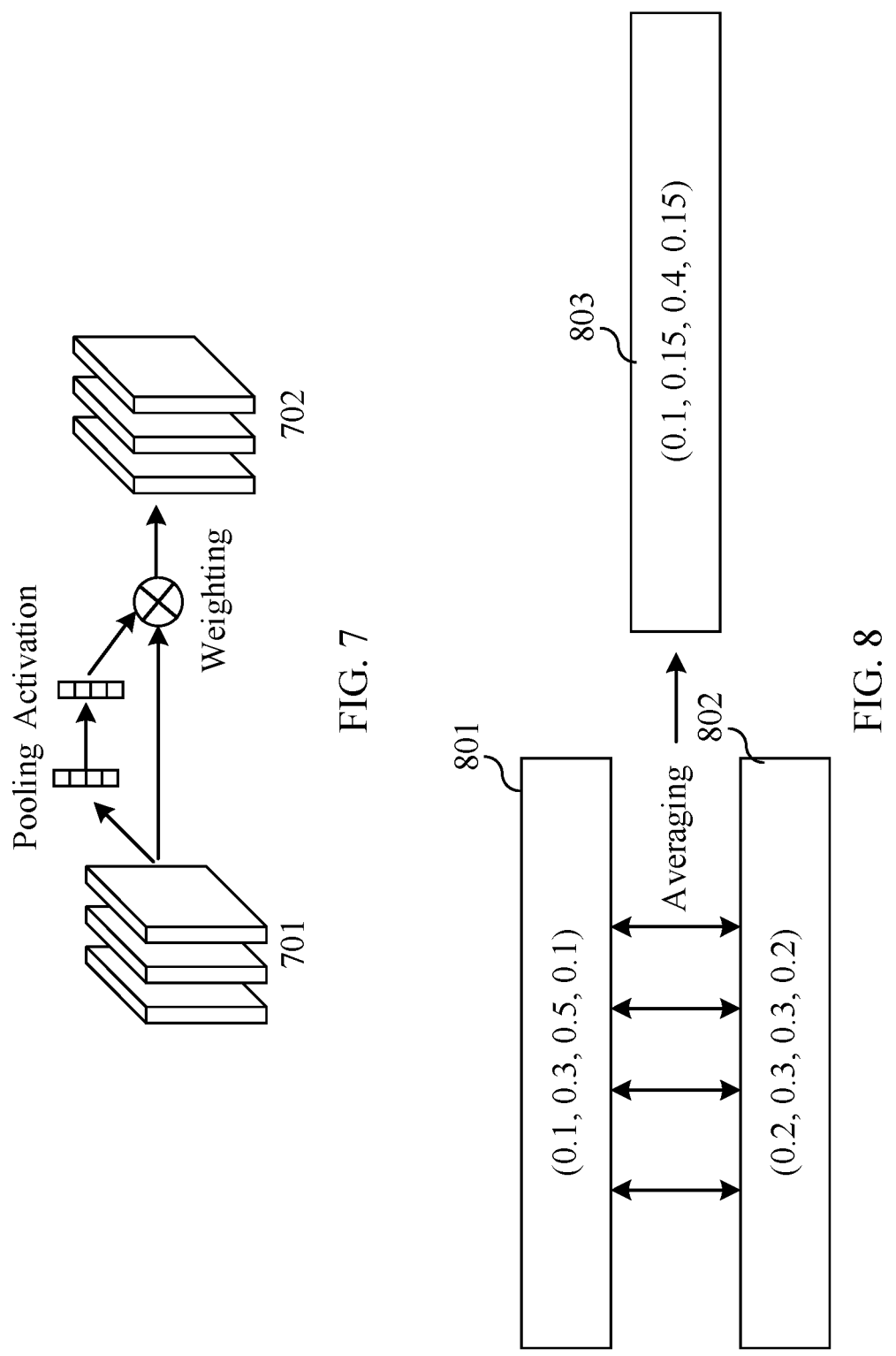
FIG. 7 is a schematic diagram of a channel attention mechanism in the embodiment shown in FIG. 4.
FIG. 8 is a schematic diagram of combining motor imagery probability distributions in the embodiment shown in FIG. 4.

FIG. 7 is a schematic diagram of a channel attention mechanism in the embodiments of this application. As shown in FIG. 7, for a feature map 701 with a channel of C and a size of W×H, average pooling is first performed on each feature map to obtain an average of C feature maps. The average is mapped through one fully connected layer to form a channel attention value. An activation function of the fully connected layer is a sigmoid function. Finally, the channel attention value is multiplied by a corresponding channel feature map, to form a channel attention feature map 702.

In the embodiments of this application, the channel attention mechanism may be applied to electrode channels in the first sample electroencephalogram signal. That is, the image features of the electrode channels in the first sample electroencephalogram signal are respectively processed using the first channel attention weighting module, to obtain weights of the electrode channels in the first sample electroencephalogram signal, and image feature values of the electrode channels in the first sample electroencephalogram signal are respectively weighted according to the weights of the electrode channels, to obtain a weighted feature map.

In a possible embodiment, the computer device obtains a loss function value of the first sample electroencephalogram signal based on the probability distribution of the first sample electroencephalogram signal and the motor imagery type of the first sample electroencephalogram signal, and trains the first electroencephalogram signal classification model based on the loss function value of the first sample electroencephalogram signal.

In a possible embodiment, the computer device obtains a first loss function value of the first sample electroencephalogram signal based on the probability distribution of the first sample electroencephalogram signal and the motor imagery type of the first sample electroencephalogram signal; and obtains a second loss function value of the first sample electroencephalogram signal based on the feature vector of the first sample electroencephalogram signal and a feature vector of the motor imagery type, and obtains the loss function value of the first sample electroencephalogram signal based on the first loss function value and the second loss function value.

The first loss function value is a multi-class cross-entropy loss function value obtained based on the probability distribution of the first sample electroencephalogram signal and the motor imagery type of the first sample electroencephalogram signal. The second loss function value is a central loss function value obtained based on the feature vector of the first sample electroencephalogram signal and a center vector of the motor imagery type of the first sample electroencephalogram signal.

In a possible embodiment, the center vector of the motor imagery type of the first sample electroencephalogram signal is obtained based on feature vectors of all sample electroencephalogram signals of the motor imagery type.

In a possible embodiment, the computer device obtains feature vectors of all sample electroencephalogram signals of the motor imagery type of the first sample electroencephalogram signal, and averages the feature vectors of all the sample electroencephalogram signals of the motor imagery type of the first sample electroencephalogram signal to obtain the center vector of the motor imagery type of the first sample electroencephalogram signal.

This technical solution may include two loss functions: a classifier loss function (that is, used for obtaining the first loss function value) and a center loss function (that is, used for obtaining the second loss function value).

The classifier loss function is shown as follows:

$$L(\theta_f) = E_{(x,y) \sim D} L(p, y)$$

where p and y are respectively a prediction probability and an actual label of training data, L represents a cross entropy loss function, $\theta_f$ represents an overall network parameter, and $E_{(x,y) \sim D}$ is an expectation of training data.

To ensure that the features extracted by the model have strong divisibility, in this application, a center loss is calculated according to flattened features and classes of the features. The center loss function is shown as follows:

$$L_c(\theta_f) = 0.5 \sum_{i=1}^{m} \left\| x_i - c_{y_i} \right\|_2^2$$

where $x_i$ and $c_{y_i}$ are respectively feature centers of extended features and classes.

An overall loss function in this technical solution is:

$$L_{total}(\theta_f) = L + \alpha L_c$$

where $\alpha$ is a hyperparameter for balancing a classification loss L and a Center Loss loss $L_c$.

In the embodiments of this application, parameters of the neural network model may be solved using an Adam-based gradient descent method, and the parameters of the model are initialized using Xavier. In a solving process, each EEG signal under test and a corresponding label are sent into the network for learning, and the model is optimized through error backpropagation.

In a possible embodiment, in response to that the at least two electroencephalogram signal classification models include a first electroencephalogram signal classification model and the first electroencephalogram signal classification model has been trained a specified number of rounds, the first electroencephalogram signal classification model is verified using a verification electroencephalogram signal of the first electroencephalogram signal classification model, to obtain the accuracy of the first electroencephalogram signal classification model, and in response to that the accuracy of the first electroencephalogram signal classification model is greater than an accuracy threshold, the first electroencephalogram signal classification model is determined as the trained first electroencephalogram signal classification model.

In a possible embodiment, the verification electroencephalogram signal is inputted into the first electroencephalogram signal classification model to obtain a probability distribution of the verification electroencephalogram signal; and the accuracy of the first electroencephalogram signal classification model is determined based on the probability distribution of the verification electroencephalogram signal and the motor imagery type of the verification electroencephalogram signal.

The accuracy of the verification electroencephalogram signal may be a probability value of the motor imagery type of the verification electroencephalogram signal in the probability distribution of the verification electroencephalogram signal. When the probability value of the motor imagery type of the verification electroencephalogram signal in the probability distribution of the verification electroencephalogram signal is larger, it indicates that the type prediction of the verification electroencephalogram signal by the first electroencephalogram signal classification model is more accurate. When the probability value (the accuracy) is greater than the accuracy threshold, it may be considered that the first electroencephalogram signal classification model has been successfully trained.

In a possible embodiment, in response to that the accuracy of the first electroencephalogram signal classification model is less than the accuracy threshold, the first electroencephalogram signal classification model is trained again based on a training sample subset of the first electroencephalogram signal classification model. After a specified number of rounds of training again, the first electroencephalogram signal classification model is verified again using a verification electroencephalogram signal of the first electroencephalogram signal classification model.

Step 404: Obtain a first electroencephalogram signal.

In a possible embodiment, the first electroencephalogram signal includes at least two electrode signals.

The foregoing first electroencephalogram signal and the sample electroencephalogram signal are acquired and processed in similar manners. Details are not described herein again.

Step 405: Process the first electroencephalogram signal respectively using at least two electroencephalogram signal classification models to obtain respective motor imagery probability distributions from the at least two electroencephalogram signal classification models.

The motor imagery probability distributions outputted by the at least two electroencephalogram signal classification models are respective motor imagery probability distributions from the at least two electroencephalogram signal classification models after the first electroencephalogram signal is respectively inputted into the at least two electroencephalogram signal classification models. That is, the probability distributions from the at least two electroencephalogram signal classification models are used for indicating respective classification results of motor imagery of the at least two electroencephalogram signal classification models after the first electroencephalogram signal is determined using the at least two electroencephalogram signal classification models.

In a possible embodiment, in response to that the at least two electroencephalogram signal classification models include a first electroencephalogram signal classification model, the first electroencephalogram signal classification model includes a first channel attention weighting module, a first temporal convolutional layer, a first spatial convolutional layer, a first activation layer, and a first fully connected layer; processing is performed based on the first electroencephalogram signal using the first channel attention weighting module to obtain a first weighted feature map; processing is performed based on the first weighted feature map using the first temporal convolutional layer to obtain a first temporal feature map, the first temporal convolutional layer being configured to extract a temporal feature of an electroencephalogram signal; processing is performed based on the first temporal feature map using the first spatial convolutional layer to obtain a first spatial feature map; the first spatial convolutional layer is configured to extract spatial features of different areas of the brain of an object of the electroencephalogram signal; data processing is performed based on the first spatial feature map using the first activation layer to obtain a first activation feature map; data processing is performed based on the first activation feature map using the first fully connected layer to obtain a probability distribution that is of the first electroencephalogram signal and is outputted by the first electroencephalogram signal classification model.

In a possible embodiment, data processing is performed based on the first activation feature map using the first fully connected layer to obtain a feature vector of the first electroencephalogram signal, and a probability distribution of the first electroencephalogram signal is obtained based on the feature vector of the first electroencephalogram signal.

After data processing is performed on the first activation feature map using the first fully connected layer, the first fully connected layer may output the feature vector of the first electroencephalogram signal. In this case, the feature vector is normalized, so that a normalized feature vector with a sum of values in the dimensions being 1. In this case, the value in each dimension of the normalized feature vector respectively represents a probability of a motor imagery type. Therefore, the values of the dimensions of the normalized feature vector together form the probability distribution of the first electroencephalogram signal.

Step 406: Determine a motor imagery type of the first electroencephalogram signal based on the respective motor imagery probability distributions from the at least two electroencephalogram signal classification models.

In a possible embodiment, a motor imagery probability distribution of the first electroencephalogram signal is obtained based on the respective motor imagery probability distributions from the at least two electroencephalogram signal classification models, the motor imagery probability distribution of the first electroencephalogram signal including probability values of motor imagery types; and the motor imagery type of the first electroencephalogram signal is determined based on the motor imagery probability distribution of the first electroencephalogram signal.

The motor imagery probability distribution of the first electroencephalogram signal includes probability values of motor imagery types.

In a possible embodiment, a motor imagery type with a maximum probability value in the motor imagery probability distributions of the first electroencephalogram signal is determined as the motor imagery type of the first electroencephalogram signal.

In a possible embodiment, in response to that a maximum probability value in the motor imagery probability distribution of the first electroencephalogram signal is greater than a probability threshold, the motor imagery type with a maximum probability value is determined as the motor imagery type of the first electroencephalogram signal.

For example, when the maximum probability value in the motor imagery probability distribution of the first electroencephalogram signal is 0.4, the probability threshold is 0.5 in this case, and the maximum probability value is less than the probability threshold. In this case, no probability value in the motor imagery probability distribution of the first electroencephalogram signal is greater than the probability threshold. Therefore, the motor imagery type of the first electroencephalogram signal is determined as "unrecognizable". When the maximum probability value in the motor imagery probability distribution of the first electroencephalogram signal is 0.7 and the probability threshold is 0.5, in this case, the motor imagery type of the maximum probability value of 0.7 is determined as the motor imagery type of the first electroencephalogram signal.

In a possible embodiment, the respective motor imagery probability distributions from the at least two electroencephalogram signal classification models are combined based on the motor imagery type, to obtain the motor imagery probability distribution.

In a possible embodiment, the motor imagery probability distributions outputted by the electroencephalogram signal classification models include probability values of motor imagery types, and weighted summation is performed on the probability values of the motor imagery types in the respective motor imagery probability distributions from the at least two electroencephalogram signal classification models based on the motor imagery type, to obtain probability values of the first electroencephalogram signal and the motor imagery types; and the motor imagery probability distribution is obtained based on the probability values of the first electroencephalogram signal and the motor imagery types.

In a possible embodiment, the accuracies of the electroencephalogram signal classification models are obtained; and weighted summation is performed on the probability values of the motor imagery types in the respective motor imagery probability distributions from the at least two electroencephalogram signal classification models based on the accuracies of the electroencephalogram signal classification models and the motor imagery type, to obtain probability values of the first electroencephalogram signal and the motor imagery types.

In a possible embodiment, the accuracies of the electroencephalogram signal classification models are used for indicating weights occupied by probability values of the motor imagery types in the motor imagery probability distributions outputted by the electroencephalogram signal classification models in a process of weighted summation.

In a possible embodiment, in a training process, the model training device verifies the electroencephalogram signal classification models based on the verification electroencephalogram signals of the electroencephalogram signal classification models, to determine the accuracies of the electroencephalogram signal classification models. That is, during the verification of the electroencephalogram signal classification models using the verification electroencephalogram signals, an electroencephalogram signal classification model with a higher accuracy usually has a better training effect. Therefore, a probability distribution outputted by the electroencephalogram signal classification model with a higher accuracy is more reliable and can have a larger weight ratio in the process of weighted summation.

In a possible embodiment, the probability values of the motor imagery types in the respective motor imagery probability distributions from the at least two electroencephalogram signal classification models are averaged based on the motor imagery type, to obtain probability values of the first electroencephalogram signal and the motor imagery types.

FIG. 8 is a schematic diagram of combining motor imagery probability distributions in this application. As shown in FIG. 8, for example, the electroencephalogram signal classification model includes a first electroencephalogram signal classification model and a second electroencephalogram signal classification model. A first motor imagery probability distribution 801 is a probability distribution outputted by the first electroencephalogram signal classification model based on a first electroencephalogram signal. A second motor imagery probability distribution 802 is a probability distribution outputted by the second electroencephalogram signal classification model based on the first electroencephalogram signal. In this case, (0.1, 0.3, 0.5, 0.1) in the first motor imagery probability distribution 801 respectively indicate probabilities of four motor imagery types (A, B, C, D) corresponding to the first electroencephalogram signal, and (0.2, 0.3, 0.3, 0.2) in the second motor imagery probability distribution 802 respectively indicate probabilities of four motor imagery types (A, B, C, D) corresponding to the first electroencephalogram signal. In this case, probabilities of the same type in the first motor imagery probability distribution 801 and the second motor imagery probability distribution 802 are averaged to obtain a motor imagery probability distribution 803 of the first electroencephalogram signal.

In a possible embodiment, a motor imagery type with a maximum probability value in the respective motor imagery probability distributions from the at least two electroencephalogram signal classification models is determined as the motor imagery type of the first electroencephalogram signal.

After the respective motor imagery probability distributions from the at least two electroencephalogram signal classification models are obtained, a motor imagery type with a maximum probability value in all probability values included in the respective motor imagery probability distributions from the at least two electroencephalogram signal classification models may be determined as the motor imagery type of the first electroencephalogram signal.

That is, during classification of a new EEG data sample using n optimized electroencephalogram signal classification models, the sample is first inputted into submodels for prediction to obtain n predicted probabilities. When n predicted probabilities are added and averaged to obtain a final predicted probability to perform classification, the integration manner is referred to as "average integration". When a class corresponding to a maximum probability in the n predicted probabilities is used as a final class of classification, the integration manner is referred to as "maximum integration". During actual application, one of the two integration manners is selected according to a specific signal under test.

In summary, in the solution in the embodiments of this application, a plurality of electroencephalogram signal classification models are trained based on augmented data sets obtained by performing data augmentation on different training subsets of the same training sample set, an electroencephalogram signal is processed using the plurality of trained electroencephalogram signal classification models to obtain probability distributions outputted by the plurality of electroencephalogram signal classification models, and a motor imagery type of the electroencephalogram signal is determined according to the probability distributions outputted by the plurality of electroencephalogram signal classification models. In the foregoing solution, different sample subsets are obtained from one training sample set, and at least two electroencephalogram signal classification models are trained after data augmentation. In a prediction process, the same electroencephalogram signal is classified respectively using the at least two electroencephalogram signal classification models, so that a motor imagery type of the electroencephalogram signal is obtained by combining respective output results of the at least two electroencephalogram signal classification models. That is, for a relatively small number of training samples, a training sample set is divided into a plurality of subsets before data augmentation. A plurality of electroencephalogram signal classification models are respectively trained using an augmented data set obtained through augmentation. During prediction, a motor imagery type is respectively determined for an output result of an electroencephalogram signal by combining the plurality of electroencephalogram signal classification models, thereby improving the accuracy of classifying an electroencephalogram signal using a model trained with a relatively small number of training samples.

Figure 9:
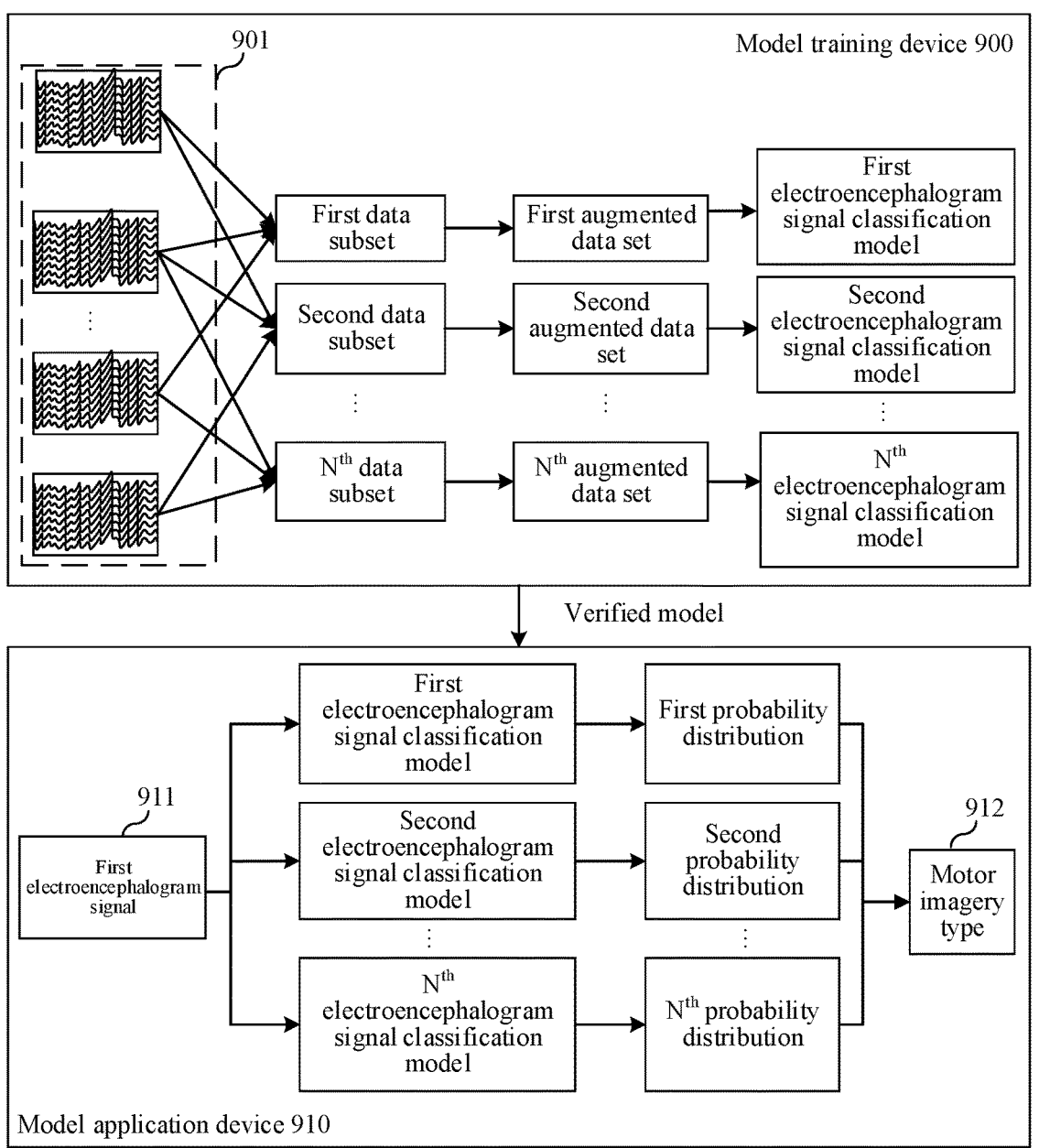
FIG. 9 is a block flowchart of electroencephalogram signal classification according to an exemplary embodiment.

FIG. 9 is a block flowchart of electroencephalogram signal classification according to an exemplary embodiment. In the embodiments of this application, the electroencephalogram signal classification includes a model training process and a model application process. The model training process and the model application process may be jointly performed by a model training device 900 and a model application device (that is, the signal processing device) 910. As shown in FIG. 9, the model training process and the model application process are as follows:

In the model training device 900, the model training device obtains a first training sample set 901 used for training electroencephalogram signal classification models. The first training sample set 901 includes N sample electroencephalogram signals used for training and motor imagery types of the N sample electroencephalogram signals.

Before training the electroencephalogram signal classification models, the model training device needs to determine training sets for the electroencephalogram signal classification models. A training process of the first electroencephalogram signal classification model is used as an example. When needing to train the first electroencephalogram signal classification model, the model training device may first select a verification electroencephalogram signal of the first electroencephalogram signal classification model from the sample electroencephalogram signals in the first training sample set 901, so that after training, the first electroencephalogram signal classification model is verified using the verification electroencephalogram signal.

A training set (that is, a first data subset) of the first electroencephalogram signal classification model may be constructed based on all sample electroencephalogram signals different from the verification electroencephalogram signal of the first electroencephalogram signal classification model. For example, the verification electroencephalogram signal of the first electroencephalogram signal classification model is an $N^{th}$ sample electroencephalogram signal. The first data subset includes all sample electroencephalogram signals different from the $N^{th}$ sample electroencephalogram signal in the first training sample set and motor imagery types of the sample electroencephalogram signals.

There is usually a relatively small amount of sample data of the motor imagery types. Therefore, a quantity of samples for model training needs to be increased through data augmentation. That is, data augmentation may be performed on training sets of electroencephalogram signal classification models to obtain augmented data sets of the training sets of the electroencephalogram signal classification models, and the electroencephalogram signal classification models are respectively trained using the augmented data sets of the electroencephalogram signal classification models, to obtain trained electroencephalogram signal classification models.

After the electroencephalogram signal classification models have been trained predetermined rounds, the model training device 900 may verify the electroencephalogram signal classification models using the verification electroencephalogram signals of the electroencephalogram signal classification models, and verified electroencephalogram signal classification models are sent to a model application device to implement classification of an electroencephalogram signal.

In the model application device 910, an obtained first electroencephalogram signal 911 is respectively inputted into the electroencephalogram signal classification models (for example, a first electroencephalogram signal classification model, a second electroencephalogram signal classification model, . . . , and an $N^{th}$ electroencephalogram signal classification model), to respectively obtain probability distributions outputted by the electroencephalogram signal classification models, and a motor imagery type 912 of the first electroencephalogram signal is obtained in the foregoing average integration or maximum integration manner according to the probability distributions outputted by the electroencephalogram signal classification models.

Figure 10:
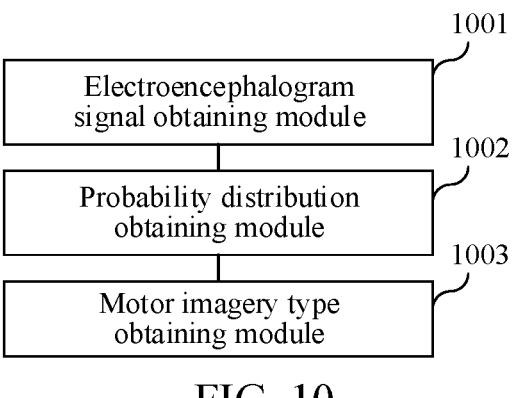
FIG. 10 is a structural block diagram of an electroencephalogram signal classification apparatus according to an exemplary embodiment.

FIG. 10 is a structural block diagram of an electroencephalogram signal classification apparatus according to an exemplary embodiment. The electroencephalogram signal classification apparatus may implement all or some steps in the method provided in the embodiment shown in FIG. 2 or FIG. 4. The electroencephalogram signal classification apparatus includes:

an electroencephalogram signal obtaining module 1001, configured to obtain a first electroencephalogram signal;

a probability distribution obtaining module 1002, configured to process the first electroencephalogram signal respectively using at least two electroencephalogram signal classification models to obtain respective motor imagery probability distributions from the at least two electroencephalogram signal classification models, each electroencephalogram signal classification model being a machine learning model trained using an augmented data set, the augmented data set being a data set obtained by performing data augmentation on a training sample subset, the training sample subset including a sample electroencephalogram signal different from a verification electroencephalogram signal of the electroencephalogram signal classification model in a first training sample set, the first training sample set including at least two sample electroencephalogram signals and motor imagery types of the at least two sample electroencephalogram signals, the verification electroencephalogram signal being a sample electroencephalogram signal used for verifying the electroencephalogram signal classification model, the at least two electroencephalogram signal classification models respectively having different verification electroencephalogram signals in the first training sample set; and a motor imagery type obtaining module 1003, configured to determine a motor imagery type of the first electroencephalogram signal based on the respective motor imagery probability distributions from the at least two electroencephalogram signal classification models.

In a possible embodiment, the motor imagery type obtaining module 1003 includes:

an electroencephalogram probability distribution obtaining submodule, configured to obtain a motor imagery probability distribution of the first electroencephalogram signal based on the respective motor imagery probability distributions from the at least two electroencephalogram signal classification models, the probability distribution of the first electroencephalogram signal including probability values respectively corresponding to motor imagery types; and a motor imagery type obtaining submodule, configured to determine the motor imagery type of the first electroencephalogram signal based on the motor imagery probability distribution of the first electroencephalogram signal.

In a possible embodiment, the electroencephalogram probability distribution obtaining submodule is further configured to:

combine the respective motor imagery probability distributions from the at least two electroencephalogram signal classification models based on the motor imagery type, to obtain the motor imagery probability distribution of the first electroencephalogram signal.

In a possible embodiment, the motor imagery probability distributions outputted by the electroencephalogram signal classification models include probability values of motor imagery types; and the electroencephalogram probability distribution obtaining submodule is further configured to:

perform weighted summation on the respective motor imagery probability distributions from the at least two electroencephalogram signal classification models based on the motor imagery type, to obtain the motor imagery probability distribution of the first electroencephalogram signal.

In a possible embodiment, the motor imagery type obtaining module 1003 is further configured to:

determine a motor imagery type with a maximum probability value in the respective motor imagery probability distributions from the at least two electroencephalogram signal classification models as the motor imagery type of the first electroencephalogram signal.

In a possible embodiment, in response to that the at least two electroencephalogram signal classification models include a first electroencephalogram signal classification model, the first electroencephalogram signal classification model includes a first channel attention weighting module, a first temporal convolutional layer, a first spatial convolutional layer, a first activation layer, and a first fully connected layer; and the probability distribution obtaining module 1002 includes:

a first weighting submodule, configured to process the first electroencephalogram signal using the first channel attention weighting module to obtain a first weighted feature map;

a first temporal extraction submodule, configured to process the first weighted feature map using the first temporal convolutional layer to obtain a first temporal feature map, the first temporal convolutional layer being configured to extract a temporal feature of an electroencephalogram signal;

a first spatial extraction submodule, configured to process the first temporal feature map using the first spatial convolutional layer to obtain a first spatial feature map, the first spatial convolutional layer being configured to extract spatial features of different areas of the brain of an object corresponding to the electroencephalogram signal;

a first activation submodule, configured to process the first spatial feature map using the first activation layer to obtain a first activation feature map; and a first probability distribution obtaining submodule, configured to process the first activation feature map using the first fully connected layer to obtain the motor imagery probability distribution that is of the first electroencephalogram signal and is outputted by the first electroencephalogram signal classification model.

In a possible embodiment, the apparatus further includes:

a first sample set obtaining module, configured to obtain the first training sample set;

a first sample subset obtaining module, configured to obtain a first training sample subset based on a sample electroencephalogram signal different from a verification electroencephalogram signal of the first electroencephalogram signal classification model in the first training sample set, the first training sample subset including a first sample electroencephalogram signal;

a data augmentation module, configured to perform data augmentation based on the first training sample subset to obtain a first augmented data set, the first augmented data set including the first sample electroencephalogram signal, a first augmented signal of the first sample electroencephalogram signal, and a motor imagery type of the first sample electroencephalogram signal; and a first training module, configured to train the first electroencephalogram signal classification model based on the first augmented data set.

In a possible embodiment, the data augmentation module includes:

an augmentation factor obtaining submodule, configured to obtain an augmentation factor of the first training sample subset, the augmentation factor being used for indicating a scaling ratio of a sample in the training sample subset; and a data augmentation submodule, configured to scale the first sample electroencephalogram signal based on the augmentation factor of the first training sample subset to obtain the first augmented signal of the first sample electroencephalogram signal.

In a possible embodiment, the apparatus further includes:

a verification signal obtaining module, configured to determine the verification electroencephalogram signal of the first electroencephalogram signal classification model from the at least two sample electroencephalogram signals in the first training sample set based on the first electroencephalogram signal classification model.

In summary, in the solution in the embodiments of this application, a plurality of electroencephalogram signal classification models are trained based on augmented data sets obtained by performing data augmentation on different training subsets of the same training sample set, an electroencephalogram signal is processed using the plurality of trained electroencephalogram signal classification models to obtain probability distributions outputted by the plurality of electroencephalogram signal classification models, and a motor imagery type of the electroencephalogram signal is determined according to the probability distributions outputted by the plurality of electroencephalogram signal classification models. In the foregoing solution, different sample subsets are obtained from one training sample set, and at least two electroencephalogram signal classification models are trained after data augmentation. In a prediction process, the same electroencephalogram signal is classified respectively using the at least two electroencephalogram signal classification models, so that a motor imagery type of the electroencephalogram signal is obtained by combining respective output results of the at least two electroencephalogram signal classification models. That is, for a relatively small number of training samples, a training sample set is divided into a plurality of subsets before data augmentation. A plurality of electroencephalogram signal classification models are respectively trained using an augmented data set obtained through augmentation. During prediction, a motor imagery type is respectively determined for an output result of an electroencephalogram signal by combining the plurality of electroencephalogram signal classification models, thereby improving the accuracy of classifying an electroencephalogram signal using a model trained with a relatively small number of training samples.

Figure 11:
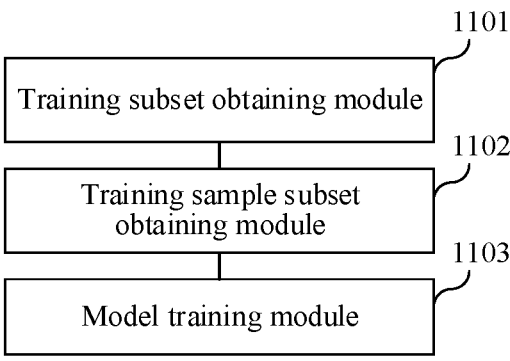
FIG. 11 is a structural block diagram of an electroencephalogram signal classification apparatus according to an exemplary embodiment.

FIG. 11 is a structural block diagram of an electroencephalogram signal classification apparatus according to an exemplary embodiment. The electroencephalogram signal classification apparatus may implement all or some steps in the method provided in the embodiment shown in FIG. 3 or FIG. 4. The electroencephalogram signal classification apparatus includes:

a training subset obtaining module 1101, configured to obtain a first training sample set, the first training sample set including at least two sample electroencephalogram signals and motor imagery types of the at least two sample electroencephalogram signals;

a training sample subset obtaining module 1102, configured to obtain respective training sample subsets of at least two electroencephalogram signal classification models based on the first training sample set, each training sample subset including a sample electroencephalogram signal different from a verification electroencephalogram signal of each electroencephalogram signal classification model in the first training sample set, the at least two electroencephalogram signal classification models have respectively different sample electroencephalogram signals in the first training sample set, the first training sample set including the at least two sample electroencephalogram signals and the motor imagery types of the at least two sample electroencephalogram signals, the verification electroencephalogram signal being a sample electroencephalogram signal used for verifying the electroencephalogram signal classification model, the at least two electroencephalogram signal classification models respectively having different verification electroencephalogram signals in the first training sample set; and a model training module 1103, configured to train respective electroencephalogram signal classification models of at least two training sample subsets based on at least two augmented data sets to obtain at least two trained electroencephalogram signal classification models, the at least two augmented data sets being data sets obtained by performing data augmentation on the respective training sample subsets of the at least two electroencephalogram signal classification models, where the at least two trained electroencephalogram signal classification models are configured to perform data processing on a first electroencephalogram signal to obtain respective motor imagery probability distributions from the at least two electroencephalogram signal classification models, the motor imagery probability distributions from the at least two electroencephalogram signal classification models being used for determining a motor imagery type of the first electroencephalogram signal.

In a possible embodiment, the training sample subset obtaining module 1102 includes:

a verification signal obtaining submodule, configured to determine the respective verification electroencephalogram signals of the at least two electroencephalogram signal classification models from the at least two sample electroencephalogram signals in the first training sample set based on the at least two electroencephalogram signal classification models; and a training sample subset obtaining submodule 1102, configured to obtain the respective training sample subsets of the at least two electroencephalogram signal classification models based on the respective verification electroencephalogram signals of the at least two electroencephalogram signal classification models and the first training sample set.

In summary, in the solution in the embodiments of this application, a plurality of electroencephalogram signal classification models are trained based on augmented data sets obtained by performing data augmentation on different training subsets of the same training sample set, an electroencephalogram signal is processed using the plurality of trained electroencephalogram signal classification models to obtain probability distributions outputted by the plurality of electroencephalogram signal classification models, and a motor imagery type of the electroencephalogram signal is determined according to the probability distributions outputted by the plurality of electroencephalogram signal classification models. In the foregoing solution, different sample subsets are obtained from one training sample set, and at least two electroencephalogram signal classification models are trained after data augmentation. In a prediction process, the same electroencephalogram signal is classified respectively using the at least two electroencephalogram signal classification models, so that a motor imagery type of the electroencephalogram signal is obtained by combining respective output results of the at least two electroencephalogram signal classification models. That is, for a relatively small number of training samples, a training sample set is divided into a plurality of subsets before data augmentation. A plurality of electroencephalogram signal classification models are respectively trained using an augmented data set obtained through augmentation. During prediction, a motor imagery type is respectively determined for an output result of an electroencephalogram signal by combining the plurality of electroencephalogram signal classification models, thereby improving the accuracy of classifying an electroencephalogram signal using a model trained with a relatively small number of training samples.

Figure 12:
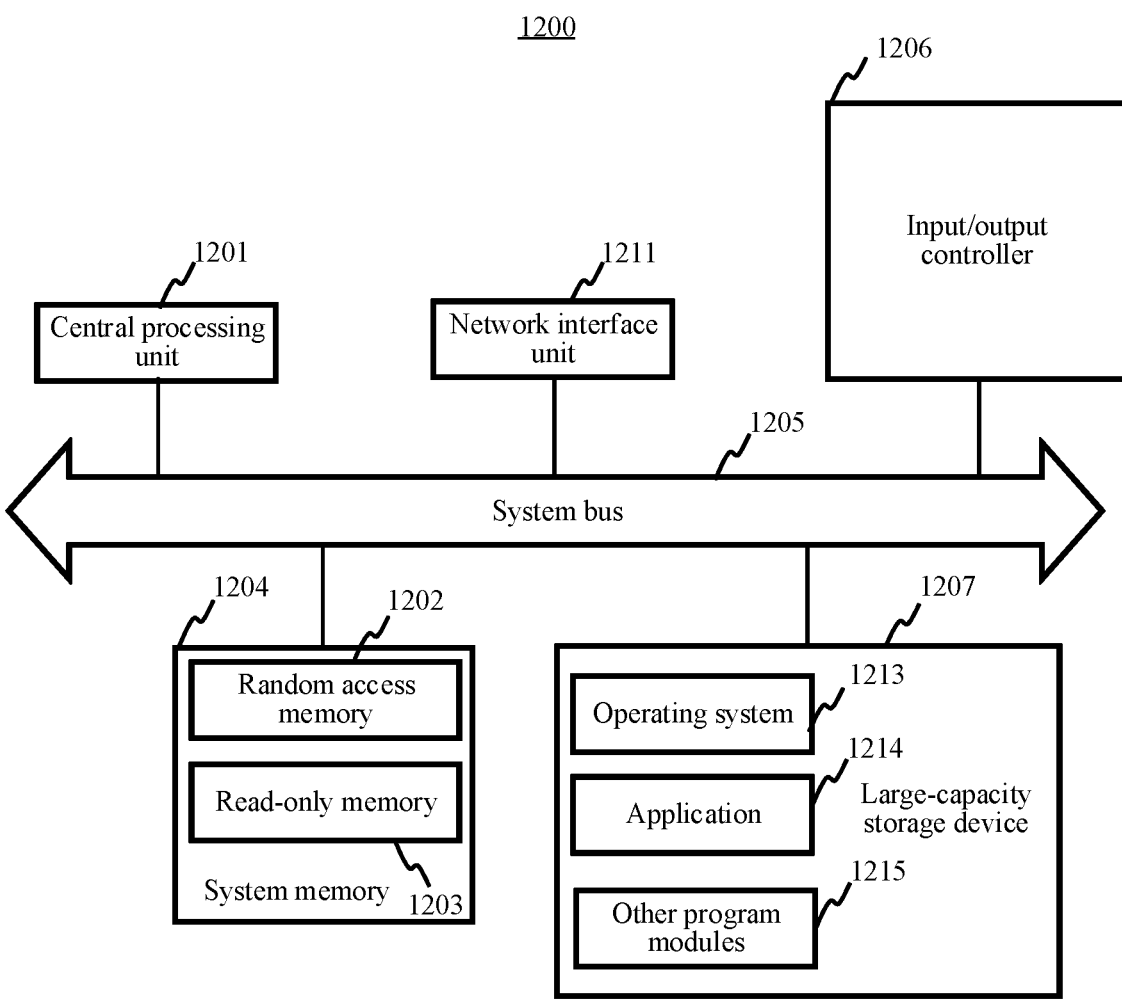
FIG. 12 is a schematic structural diagram of a computer device according to an exemplary embodiment.

FIG. 12 is a schematic structural diagram of a computer device according to an exemplary embodiment. The computer device may be implemented as the model training device and/or the signal processing device in the foregoing method embodiments. The computer device 1200 includes a central processing unit (CPU) 1201, a system memory 1204 including a random access memory (RAM) 1202 and a read-only memory (ROM) 1203, and a system bus 1205 connecting the system memory 1204 to the CPU 1201. The computer device 1200 further includes a basic input/output system 1206 configured to transmit information between components in the computer, and a mass storage device 1207 configured to store an operating system 1213, an application program 1214, and another program module 1215.

The mass storage device 1207 is connected to the central processing unit 1201 through a mass storage controller (not shown) connected to the system bus 1205. The mass storage device 1207 and an associated computer-readable medium provide non-volatile storage for the computer device 1200. That is, the mass storage device 1207 may include a computer-readable medium (not shown) such as a hard disk or a compact disc read only memory (CD-ROM) drive.

In general, the computer-readable medium may include a computer storage medium and a communication medium. The computer storage medium includes volatile and non-volatile, removable and non-removable media that are configured to store information such as computer-readable instructions, data structures, program modules, or other data and that are implemented using any method or technology. The computer storage medium includes a RAM, a ROM, a flash memory or another solid-state memory technology, a CD-ROM or another optical memory, a magnetic cassette, a magnetic tape, a magnetic disk memory, or another magnetic storage device. Certainly, those skilled in the art may learn that the computer storage medium is not limited to the above. The foregoing system memory 1204 and mass storage device 1207 may be collectively referred to as a memory.

The computer device 1200 may be connected to the Internet or another network device using a network interface unit 1211 connected to the system bus 1205.

The memory further includes one or more computer instructions. The one or more computer instructions are stored in the memory. The CPU 1201 executes the one or more computer instructions to implement all or some of steps of the method shown in FIG. 2, FIG. 3 or FIG. 4.

In an exemplary embodiment, a non-temporary computer-readable storage medium including an instruction, for example, a memory including a computer program (an instruction), is further provided, and the program (the instruction) may be executed by a processor in a computer device to complete the method shown in the embodiments of this application. For example, the non-transitory computer readable storage medium may be a read-only memory (ROM), a random access memory (RAM), a CD-ROM, a tape, a floppy disk, an optical data storage device, or the like.

In sum, the term "unit" or "module" in this application refers to a computer program or part of the computer program that has a predefined function and works together with other related parts to achieve a predefined goal and may be all or partially implemented by using software, hardware (e.g., processing circuitry and/or memory configured to perform the predefined functions), or a combination thereof. Each unit or module can be implemented using one or more processors (or processors and memory). Likewise, a processor (or processors and memory) can be used to implement one or more modules or units. Moreover, each module or unit can be part of an overall module that includes the functionalities of the module or unit.

In an exemplary embodiment, a computer program product or a computer program is provided. The computer program product or the computer program includes computer instructions, and the computer instructions are stored in a computer-readable storage medium. A processor of a computer device reads the computer instructions from the computer-readable storage medium, and executes the computer instructions, to cause the computer device to perform the foregoing method in the embodiments.

What is claimed is:

1. An electroencephalogram signal classification method, performed by a computer device, the method comprising:
   obtaining a first electroencephalogram signal;
   processing, using at least two electroencephalogram signal classification models, the first electroencephalogram signal to obtain respective motor imagery probability distributions from the at least two electroencephalogram signal classification models, wherein each electroencephalogram signal classification model is a machine learning model trained using an augmented data set; and
   determining a motor imagery type of the first electroencephalogram signal based on the motor imagery probability distributions including obtaining a motor imagery probability distribution of the first electroencephalogram signal based on the motor imagery probability distributions from the at least two electroencephalogram signal classification models, the motor imagery probability distribution of the first electroencephalogram signal comprising probability values corresponding to respective motor imagery types, wherein the at least two electroencephalogram signal classification models comprise a first electroencephalogram signal classification model having a first channel attention weighting module, a first temporal convolutional layer, a first spatial convolutional layer, a first activation layer, and a first fully connected layer; the augmented data set is obtained by performing data augmentation on a training sample subset, and the method includes:
   processing, using at least two electroencephalogram signal classification models, the first electroencephalogram signal comprises:
   processing, using the first channel attention weighting module, the first electroencephalogram signal to obtain a first weighted feature map;
   processing, using the first temporal convolutional layer, the first weighted feature map to obtain a first temporal feature map, wherein the first temporal convolutional layer is configured to extract a temporal feature of an electroencephalogram signal;

processing, using the first spatial convolutional layer, the first temporal feature map to obtain a first spatial feature map, wherein the first spatial convolutional layer is configured to extract spatial features of different areas of a brain of an object corresponding to the electroencephalogram signal;

processing, using the first activation layer, the first spatial feature map to obtain a first activation feature map; and processing, using the first fully connected layer, the first activation feature map to obtain the motor imagery probability distribution of the first electroencephalogram signal from the first electroencephalogram signal classification model.

2. The method according to claim 1, wherein determining the motor imagery type of the first electroencephalogram signal comprises:

determining the motor imagery type of the first electroencephalogram signal based on the motor imagery probability distribution of the first electroencephalogram signal.

3. The method according to claim 2, wherein obtaining the motor imagery probability distribution of the first electroencephalogram signal comprises:

obtaining the motor imagery probability distribution of the first electroencephalogram signal by combining the motor imagery probability distributions from the at least two electroencephalogram signal classification models based on the motor imagery type.

4. The method according to claim 3, wherein obtaining the motor imagery probability distribution of the first electroencephalogram signal comprises:

performing weighted summation on the motor imagery probability distributions from the at least two electroencephalogram signal classification models based on the motor imagery type to obtain the motor imagery probability distribution of the first electroencephalogram signal.

5. The method according to claim 1, wherein determining the motor imagery type of the first electroencephalogram signal comprises:

determining a motor imagery type with a maximum probability value in the motor imagery probability distributions from the at least two electroencephalogram signal classification models as the motor imagery type of the first electroencephalogram signal.

6. The method according to claim 1, wherein the training sample subset comprises a sample electroencephalogram signal different from a verification electroencephalogram signal of the electroencephalogram signal classification model in a first training sample set, the method further comprising:

obtaining the first training sample set, the first training sample set comprises at least two sample electroencephalogram signals and motor imagery types of the at least two sample electroencephalogram signals;

obtaining, from the first training sample set, a first training sample subset comprising a first sample electroencephalogram signal obtained from a sample electroencephalogram signal different from a verification electroencephalogram signal of the first electroencephalogram signal classification model;

performing data augmentation based on the first training sample subset to obtain a first augmented data set comprising the first sample electroencephalogram signal, a first augmented signal of the first sample electroencephalogram signal, and a motor imagery type of the first sample electroencephalogram signal; and training the first electroencephalogram signal classification model based on the first augmented data set.

7. The method according to claim 6, wherein performing data augmentation based on the first training sample subset to obtain a first augmented data set comprises:

obtaining an augmentation factor of the first training sample subset, wherein the augmentation factor indicates a scaling ratio of a sample in the first training sample subset; and scaling the first sample electroencephalogram signal based on the augmentation factor of the first training sample subset to obtain the first augmented signal of the first sample electroencephalogram signal.

8. The method according to claim 6, further comprising:

before obtaining the first training sample subset:

determining the verification electroencephalogram signal of the first electroencephalogram signal classification model from the at least two sample electroencephalogram signals in the first training sample set.

9. The method according to claim 1, further comprising:

obtaining a first training sample set, the first training sample set comprises at least two sample electroencephalogram signals and motor imagery types of the at least two sample electroencephalogram signals;

obtaining respective training sample subsets of the at least two electroencephalogram signal classification models based on the first training sample set, each training sample subset comprising a sample electroencephalogram signal different from a respective verification electroencephalogram signal of each electroencephalogram signal classification model in the first training sample set; and training respective electroencephalogram signal classification models of at least two training sample subsets based on at least two augmented data sets to obtain at least two trained electroencephalogram signal classification models, the at least two augmented data sets obtained by performing data augmentation on the respective training sample subsets of the at least two electroencephalogram signal classification models, wherein the at least two trained electroencephalogram signal classification models are configured to perform data processing on a first electroencephalogram signal to obtain motor imagery probability distributions from the at least two electroencephalogram signal classification models, the motor imagery probability distributions from the at least two electroencephalogram signal classification models being used for determining a motor imagery type of the first electroencephalogram signal.

10. The method according to claim 9, wherein obtaining respective training sample subsets of at least two electroencephalogram signal classification models based on the first training sample set comprises:

determining respective verification electroencephalogram signals of the at least two electroencephalogram signal classification models in the first training sample set; and obtaining the respective training sample subsets of the at least two electroencephalogram signal classification models based on the respective verification electroencephalogram signals of the at least two electroencephalogram signal classification models and the first training sample set.

11. An electronic device, comprising:

one or more processors; and memory storing one or more programs, the one or more programs comprising instructions that, when executed by the one or more processors, cause the one or more processors to perform operations comprising:

obtaining a first electroencephalogram signal;

processing, using at least two electroencephalogram signal classification models, the first electroencephalogram signal to obtain respective motor imagery probability distributions from the at least two electroencephalogram signal classification models, wherein each electroencephalogram signal classification model is a machine learning model trained using an augmented data set;

determining a motor imagery type of the first electroencephalogram signal based on the motor imagery probability distributions including obtaining a motor imagery probability distribution of the first electroencephalogram signal based on the motor imagery probability distributions from the at least two electroencephalogram signal classification models, the motor imagery probability distribution of the first electroencephalogram signal comprising probability values corresponding to respective motor imagery types, wherein the at least two electroencephalogram signal classification models comprise a first electroencephalogram signal classification model having a first channel attention weighting module, a first temporal convolutional layer, a first spatial convolutional layer, a first activation layer, and a first fully connected layer; the augmented data set is obtained by performing data augmentation on a training sample subset, and the one or more processors perform operations further comprising:

processing, using at least two electroencephalogram signal classification models, the first electroencephalogram signal comprises:

processing, using the first channel attention weighting module, the first electroencephalogram signal to obtain a first weighted feature map;

processing, using the first temporal convolutional layer, the first weighted feature map to obtain a first temporal feature map, wherein the first temporal convolutional layer is configured to extract a temporal feature of an electroencephalogram signal;

processing, using the first spatial convolutional layer, the first temporal feature map to obtain a first spatial feature map, wherein the first spatial convolutional layer is configured to extract spatial features of different areas of a brain of an object corresponding to the electroencephalogram signal;

processing, using the first activation layer, the first spatial feature map to obtain a first activation feature map; and processing, using the first fully connected layer, the first activation feature map to obtain the motor imagery probability distribution of the first electroencephalogram signal from the first electroencephalogram signal classification model.

12. The electronic device according to claim 11, wherein determining the motor imagery type of the first electroencephalogram signal comprises:

determining the motor imagery type of the first electroencephalogram signal based on the motor imagery probability distribution of the first electroencephalogram signal.

13. The electronic device according to claim 12, wherein obtaining the motor imagery probability distribution of the first electroencephalogram signal comprises:

obtaining the motor imagery probability distribution of the first electroencephalogram signal by combining the motor imagery probability distributions from the at least two electroencephalogram signal classification models based on the motor imagery type.

14. The electronic device according to claim 13, wherein obtaining the motor imagery probability distribution of the first electroencephalogram signal comprises:

performing weighted summation on the motor imagery probability distributions from the at least two electroencephalogram signal classification models based on the motor imagery type to obtain the motor imagery probability distribution of the first electroencephalogram signal.

15. The electronic device according to claim 11, wherein determining the motor imagery type of the first electroencephalogram signal comprises:

determining a motor imagery type with a maximum probability value in the motor imagery probability distributions from the at least two electroencephalogram signal classification models as the motor imagery type of the first electroencephalogram signal.

16. A non-transitory computer-readable storage medium, storing a computer program, the computer program, when executed by one or more processors of an electronic device, cause the one or more processors to perform operations comprising:

obtaining a first electroencephalogram signal;

processing, using at least two electroencephalogram signal classification models, the first electroencephalogram signal to obtain respective motor imagery probability distributions from the at least two electroencephalogram signal classification models, wherein each electroencephalogram signal classification model is a machine learning model trained using an augmented data set;

determining a motor imagery type of the first electroencephalogram signal based on the motor imagery probability distributions;

wherein the at least two electroencephalogram signal classification models comprise a first electroencephalogram signal classification model having a first channel attention weighting module, a first temporal convolutional layer, a first spatial convolutional layer, a first activation layer, and a first fully connected layer; the augmented data set is obtained by performing data augmentation on a training sample subset, and the one or more processors perform operations further comprising:

processing, using at least two electroencephalogram signal classification models, the first electroencephalogram signal comprises:

processing, using the first channel attention weighting module, the first electroencephalogram signal to obtain a first weighted feature map;

processing, using the first temporal convolutional layer, the first weighted feature map to obtain a first temporal feature map, wherein the first temporal convolutional layer is configured to extract a temporal feature of an electroencephalogram signal;

processing, using the first spatial convolutional layer, the first temporal feature map to obtain a first spatial feature map, wherein the first spatial convolutional layer is configured to extract spatial features of different areas of a brain of an object corresponding to the electroencephalogram signal;

processing, using the first activation layer, the first spatial feature map to obtain a first activation feature map; and processing, using the first fully connected layer, the first activation feature map to obtain the motor imagery probability distribution of the first electroencephalogram signal from the first electroencephalogram signal classification model.

17. The non-transitory computer-readable storage medium according to claim 16, wherein determining the motor imagery type of the first electroencephalogram signal comprises:

obtaining a motor imagery probability distribution of the first electroencephalogram signal based on the motor imagery probability distributions from the at least two electroencephalogram signal classification models, the motor imagery probability distribution of the first electroencephalogram signal comprising probability values respectively corresponding to motor imagery types; and determining the motor imagery type of the first electroencephalogram signal based on the motor imagery probability distribution of the first electroencephalogram signal based on the motor imagery probability distributions including obtaining a motor imagery probability distribution of the first electroencephalogram signal based on the motor imagery probability distributions from the at least two electroencephalogram signal classification models, the motor imagery probability distribution of the first electroencephalogram signal comprising probability values corresponding to respective motor imagery types.

18. The non-transitory computer-readable storage medium according to claim 17, wherein obtaining the motor imagery probability distribution of the first electroencephalogram signal comprises:

determining the motor imagery type of the first electroencephalogram signal based on the motor imagery probability distribution of the first electroencephalogram signal.

* * * * *